US009629808B2

(12) United States Patent
Kanamaru et al.

(10) Patent No.: US 9,629,808 B2
(45) Date of Patent: Apr. 25, 2017

(54) SUSTAINED-RELEASE SOLID PREPARATION FOR ORAL USE

(71) Applicant: Daiichi Sankyo Company, Limited, Tokyo (JP)

(72) Inventors: Taro Kanamaru, Tokyo (JP); Shinichiro Tajiri, Tokyo (JP); Sachiko Fukui, Tokyo (JP); Kazuhiro Yoshida, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/841,778

(22) Filed: Sep. 1, 2015

(65) Prior Publication Data

US 2015/0366810 A1 Dec. 24, 2015

Related U.S. Application Data

(63) Continuation of application No. 13/591,902, filed on Aug. 22, 2012, which is a continuation of application No. PCT/JP2011/053642, filed on Feb. 21, 2011.

(30) Foreign Application Priority Data

Feb. 22, 2010 (JP) ................................. 2010-035882

(51) Int. Cl.
| *A61K 9/00* | (2006.01) |
|---|---|
| *A61K 9/20* | (2006.01) |
| *A61K 9/50* | (2006.01) |
| *A61K 47/38* | (2006.01) |
| *A61K 9/70* | (2006.01) |
| *A61K 31/403* | (2006.01) |
| *A61K 31/4745* | (2006.01) |
| *A61K 31/437* | (2006.01) |
| *A61K 31/522* | (2006.01) |

(52) U.S. Cl.
CPC .......... *A61K 9/2054* (2013.01); *A61K 9/2018* (2013.01); *A61K 9/2027* (2013.01); *A61K 9/2077* (2013.01); *A61K 9/5047* (2013.01); *A61K 9/7007* (2013.01); *A61K 31/403* (2013.01); *A61K 31/437* (2013.01); *A61K 31/4745* (2013.01); *A61K 31/522* (2013.01)

(58) Field of Classification Search
CPC .. A61K 9/2054; A61K 9/5047; A61K 9/2077; A61K 9/2018; A61K 9/7007
See application file for complete search history.

(56) References Cited

U.S. PATENT DOCUMENTS

| 4,940,580 A | 7/1990 | Sangekar et al. |
|---|---|---|
| 5,547,943 A | 8/1996 | Iida et al. |
| 5,567,439 A | 10/1996 | Myers et al. |
| 5,783,212 A | 7/1998 | Fassihi |
| 5,910,319 A | 6/1999 | Anderson et al. |
| 6,224,909 B1 | 5/2001 | Opitz et al. |
| 6,287,599 B1 | 9/2001 | Burnside et al. |
| 6,485,746 B1 | 11/2002 | Campbell et al. |
| 7,138,143 B1 | 11/2006 | Mukai et al. |
| 7,576,135 B2 | 8/2009 | Ohta et al. |
| 7,910,131 B2 | 3/2011 | Bhatt et al. |
| 2001/0006649 A1 | 7/2001 | Chen |
| 2002/0054911 A1 | 5/2002 | Oh |
| 2003/0035836 A1 | 2/2003 | Shanghvi et al. |
| 2003/0198670 A1 | 10/2003 | Kumbhani et al. |
| 2004/0052844 A1 | 3/2004 | Hsiao et al. |
| 2004/0151772 A1 | 8/2004 | Andersen et al. |
| 2005/0020645 A1 | 1/2005 | Ohta et al. |
| 2005/0096365 A1 | 5/2005 | Fikstad |
| 2005/0118266 A1 | 6/2005 | Khan et al. |
| 2005/0119486 A1 | 6/2005 | Ohta et al. |
| 2005/0169994 A1 | 8/2005 | Burke et al. |
| 2005/0186276 A1 | 8/2005 | Berchielli et al. |
| 2005/0245565 A1 | 11/2005 | Ohta et al. |
| 2005/0276851 A1 | 12/2005 | Cunningham et al. |
| 2006/0008418 A1 | 1/2006 | Hansen et al. |
| 2006/0039974 A1 | 2/2006 | Akiyama et al. |
| 2006/0159753 A1 | 7/2006 | Ueki et al. |
| 2006/0280789 A1 | 12/2006 | Ueki et al. |
| 2007/0026062 A1 | 2/2007 | Holm et al. |
| 2007/0098843 A1 | 5/2007 | Tomohira |
| 2008/0004260 A1 | 1/2008 | Singh |

(Continued)

FOREIGN PATENT DOCUMENTS

| AT | WO 2005027876 A1 * | 3/2005 | ........... A61K 9/2077 |
|---|---|---|---|
| EP | 1291014 | 3/2002 | |

(Continued)

OTHER PUBLICATIONS

International Search Report issued for PCT/JP2011/053644 mailed on Apr. 12, 2011 corresponding to U.S. Appl. No. 13/591,981.
International Preliminary Report on Patentability issued for PCT/JP2011/053644 on Sep. 18, 2012 corresponding to U.S. Appl. No. 13/591,981.
Written Opinion of the International Searching Authority issued for PCT/JP2011/053644 on Apr. 12, 2011 corresponding to U.S. Appl. No. 13/591,981.
International Search Report for PCT/JP2011/053643 mailed on Apr. 12, 2011 corresponding to related U.S. Appl. No. 13/591,949.

(Continued)

Primary Examiner — Robert A Wax
Assistant Examiner — Tracy Liu
(74) Attorney, Agent, or Firm — Locke Lord LLP

(57) ABSTRACT

It is intended to avoid dose dumping of a drug and improve the dissolution properties of the drug in the lower gastrointestinal tract, and thereby provide a sustained-release matrix preparation for oral administration that reliably exhibits its main pharmacological effect when orally administered once or twice a day. The present invention provides a sustained-release matrix preparation comprising (A) a pharmacologically active drug, (B) a combination of cellulose derivatives, and (C) mannitol.

3 Claims, 23 Drawing Sheets

(56) References Cited

U.S. PATENT DOCUMENTS

| | | |
|---|---|---|
| 2008/0089937 A1 | 4/2008 | Gan et al. |
| 2008/0181947 A1 | 7/2008 | Kojima et al. |
| 2008/0187588 A1 | 8/2008 | Zuleger et al. |
| 2008/0213368 A1 | 9/2008 | Ueki et al. |
| 2008/0260815 A1 | 10/2008 | Hayes et al. |
| 2008/0268046 A1 | 10/2008 | Zuleger et al. |
| 2008/0274180 A1 | 11/2008 | Jathar et al. |
| 2009/0099151 A1 | 4/2009 | Jain et al. |
| 2009/0105491 A1 | 4/2009 | Sato et al. |
| 2009/0208579 A1 | 8/2009 | Ueki et al. |
| 2010/0081685 A1 | 4/2010 | Kojima et al. |
| 2010/0145053 A1 | 6/2010 | Patel et al. |
| 2010/0152164 A1 | 6/2010 | Ueki et al. |
| 2012/0114711 A1 | 5/2012 | Kamada |
| 2013/0004550 A1 | 1/2013 | Kanamaru et al. |
| 2013/0005763 A1 | 1/2013 | Kanamaru et al. |
| 2013/0012535 A1 | 1/2013 | Kanamaru et al. |
| 2013/0022683 A1 | 1/2013 | Kamada |
| 2013/0337064 A1 | 12/2013 | Kojima |
| 2014/0070446 A1 | 3/2014 | Kanamaru |
| 2014/0171464 A1 | 6/2014 | Ishidoh |
| 2015/0231083 A1 | 8/2015 | Yada |

FOREIGN PATENT DOCUMENTS

| | | | |
|---|---|---|---|
| EP | 1970052 | 9/2008 | |
| EP | 2105133 A1 | 9/2009 | |
| EP | 2140867 | 1/2010 | |
| JP | 63107933 | 5/1988 | |
| JP | 10330253 | 12/1998 | |
| JP | 2001513752 | 9/2001 | |
| JP | 20051513752 | 9/2001 | |
| JP | 2001270821 | 10/2001 | |
| JP | 2001522794 | 11/2001 | |
| JP | 2001524131 | 11/2001 | |
| JP | 2003507413 | 2/2003 | |
| JP | 2004026750 | 1/2004 | |
| JP | 2004518676 | 6/2004 | |
| JP | 2006507216 | 3/2006 | |
| JP | 2007537175 | 12/2007 | |
| JP | 2007537183 | 12/2007 | |
| JP | 2008169173 | 7/2008 | |
| JP | 2009500317 | 1/2009 | |
| JP | 2009532462 | 9/2009 | |
| JP | 2009535351 | 10/2009 | |
| KR | WO 2006059866 A1 * | 6/2006 | ........... A61K 9/2886 |
| WO | 9924017 | 5/1999 | |
| WO | 0113895 | 3/2001 | |
| WO | 0123000 | 4/2001 | |
| WO | 03000657 | 1/2003 | |
| WO | 03000680 | 1/2003 | |
| WO | 03016302 | 2/2003 | |
| WO | 2004058715 | 7/2004 | |
| WO | 2005000312 | 1/2005 | |
| WO | 2005048979 | 6/2005 | |
| WO | 2006006691 A2 | 1/2006 | |
| WO | 2006070781 | 7/2006 | |
| WO | 2006070930 | 7/2006 | |
| WO | 2008041553 | 4/2008 | |
| WO | 2008100107 | 8/2008 | |
| WO | 2008129846 A1 | 10/2008 | |
| WO | 2009047802 | 4/2009 | |
| WO | WO2009047802 | 4/2009 | |
| WO | 2009057138 | 5/2009 | |
| WO | 2009129300 A2 | 10/2009 | |
| WO | 2010012482 | 2/2010 | |

OTHER PUBLICATIONS

Written Opinion of the International Searching Authority issued for PCT/JP2011/053643 on Apr. 12, 2011 corresponding to related U.S. Appl. No. 13/591,949.
International Preliminary Report on Patentability issued for PCT/JP2011/053643 on Sep. 18, 2012 corresponding to related U.S. Appl. No. 13/591,949.
International Search Report issued for PCT/JP2011/053642 mailed on Apr. 12, 2011 corresponding to related U.S. Appl. No. 13/591,902.
Written Opinion of the International Searching Authority issued for PCT/JP2011/053642 on Apr. 12, 2011 corresponding to related U.S. Appl. No. 13/591,902.
International Preliminary Report on Patentability issued for PCT/JP2011/053642 on Sep. 18, 2012 corresponding to related U.S. Appl. No. 13/591,902.
Patent Abstracts of Japan—Publication No. 2001-270821; for Application No. 2000-081379, Applicant: Eisai Co., Ltd. "Powder Medicine Having Excellent Taking Easiness."
Patent Abstracts of Japan—Publication No. 2004-023750; for Application No. 2002-187913; Applicant Nippon Shinyaku Co., Ltd.: "Method for Stabilizing Medicine."
Patent Abstracts of Japan—Publication No. 2008-169173; for Application No. 2008-005439, Applicant: Kissei Pharmaceut Co., Ltd.; "Sustained Release Preparation of Carbohydrase Inhihbitor Staying in Stomach."
Ministry of Health, Labor and Welfare Food and Drug Administration Evaluation and Licensing Division, Notification, For a general name of the drug? (as translated), Japan Association for Pharmaceutical Affairs Law Foundation, PFSB/ELD No. 1111-1 (Nov. 11, 2010) (available at http://www.japal.org/contents/20101111_1111-1.pdf) (original in Japanese submitted with a machine translation).
Pre-Publication copy, Proposed INN: List 101 (tanexaban) (Later published as WHO Drug Information, vol. 23, No. 2, p. 169, 2009; available at http:///www.who.int/medicines/publications/druginformation/innlists/PL101.pdf).
Yamanouchi Pharmaceutical Co. Ltd.; "Speed with Vision," Research and development pipeline. Company World Wide Web site (https://www.astellas.com/en/ir/library/pdf/y _annual2004_eg.pdf), Feb. 11, 2004.
WHO Drug Information, vol. 18, No. 3, 2004. p. 260.
Susanne, R., et al., "Discovery of the Novel Antithrombotic Agent 5-Chloro-N-({5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor," J. Med. Chem., 2005, 48, 5900-5908.
Kubitza, D., et al., "Multiple dose escalation study investigating the pharmacodynamics, safety, and pharmacokinetic of Bay59-7939, an oral, direct Factor Xa inhibitor, in healthy male subjects." Blood, 2003. 102; Abstract 3004.
WHO Drug Information, vol. 20, No. 1, 2006, p. 38.
Pinto, DJP, et al. "Discovery of 1-(4-Methoxyphenyl)-7-oxo-6-(4-(2-oxopiperidin-1-yl)phenyl)-4,5,6,7-tetrahydro-1H-pyrazolo[3,4-c]pyridine-3-carboxamide (Apixaban, BMS-562247), a highly potent, selective, efficacious, and orally bioavalable inhibitor of blood coagulation factor Xa," J. Med. Chem., 50(22), 5339-56, 2007.
Who Drug Information, vol. 22, No. 3, 2008, pp. 226-227.
Zhang P., et al., "Discovery of betrixaban (PRT054021), N-(5-chloropyridin-2-yl)-2-(4-(N,N-dimethylcarbamimidol) benzamido)-5-methoxybenzamide, a highly potent, selective, and orally efficacious factor Xa inhibitor," Bioorg Med. Chem. Lett. 19(8), 2179-85, 2009.
Takehana, S., et al. "Antithrombotic effect of AX1826, a novel inhibitor of factor Xa, n the rat thrombosis models," Japanese Journal of Pharmacology 2000, 82 (Suppl. 1), 213P, P-375.
Kayahara, T., et al. "The in vitro Anticoagulant Activities of a Novel Selective Factor Xa Inhibitor AX1826," Japanese Journal of Pharmacology 2000, 82 (Suppl. 1), 213P, P-375.
Kayahara, T., et al. "Oral Anticoagulant Effects of a Selective FXa Inhibitor AX1826 in Cynomolgus Monkeys," Japanese Journal of Pharmacology 2000, 82 (Suppl. 1), 213P, P-376.
Just, M., et al., "A comparison of a specific factor Xa inhibitor (HMR 2906) and recombinant hirudin in a dog coronary artery thrombosis mode ," Throm Haemost, 1999, (Suppl.): Abst. 832; (XVIIth Congress of the International Society for Thromosis and Haemostasis, Washington, D.C., USA, Aug. 14-21, 1999).
Markham, R.; Aventis SA Company Presentation, "Generating greater value from our products and pipeline." (http://www.sec.gov/

(56) References Cited

OTHER PUBLICATIONS

Archives/edgar/containers/fix030/807198/000104746904003383/a2128190z6-k.hym), Feb. 5, 2004.

WHO Drug Information, vol. 16, No. 3, 2002, p. 257.

Ries, U.J., "Heterocyclic coagulation inhibitors: Design, syntheses and biological properties of orally active, dual direct thrombin and factor Xa inhibitors," American Chemical Society—226th National Meeting, New York City, NY, USA, 2003; Abst. MEDI 33.

Pruitt, J.R., et al., Discovery of 1-(2-Aminomethylphenyl)-3-trifluoromethyl-N-[3-fluoro-2'-(aminosulfonyl)(1,1'-biphenyl)]-4-yl]-1H-pyrazole-5-carboxyamide (DPC602), a Potent, Selective, and Orally Bioavailable Factor Xa Inhibitor,, J. Med. Chem., 46, 5298-5313 (2003).

Wiley, M., et al., "Non-aromatic C-amino acid-derived inhibitors of human fXa, " 228th ACS National Meeting, Philadelphia, Aug. 22-26, 2004, MEDI-252.

Wiley, M., et al., "SAR investigation of heteroatom containing non-arylglyine inhibitors of human fXa," 228th ACS National Meeting, Philadelphia, Aug. 22-26, 2004, MEDI-254.

Merriam-Webster Dictionary; Definition of "mix" (http://www.merriam-webster.com/dictionary/mix;accessedFeb. 7, 2013).

European Search Report issued in corresponding EP Application No. 11744790.4, corresponding to related U.S. Appl. No. 13/591,902 dated Mar. 21, 2014.

European Search Report issued in EP Application No. 11744791.2, corresponding to related U.S. Appl. No. 14/079,859, dated Mar. 19, 2014.

Schilling, S.U., et al., "Properties of melt extruded enteric matrix pellets," European Journak of Pharmaceutics and Biopharmaceutics, vol. 74, Isue 2, pp. 352-361 (Feb. 2010).

Kojima, M. et al., "Development of controlled release matrix pellets by annealing with micronized water—Insoluble or Enteric polymers", Journal of Controlled Release, 82-335-343 (2002).

Cheng, Y-H, et al., "Schizophrenia and Drug Delivery Systems," Journal of Drug Targeting, 8(2):107-117 (2000).

MedlinePlus, Ziprasidone (online). MedilinePlus (2009). (retrieved from the internet at http:www.nlm.nih.gov/medlineplus/druginfo/meds/a699062.html on Jul. 23, 2014).

Nippon Soda Co., Ltd., Technical Data Sheet #: TDS-01, "Hydroxypropyl Cellulose" (2011) (http://www.nissoexcipients.com/PDF/TDS-01.pdf).

European Search Report issued in European Application No. 11744792.0, corresponding to U.S. Appl. No. 13/591,981 mailed on Nov. 5, 2013.

* cited by examiner

US 9,629,808 B2

SUSTAINED-RELEASE SOLID PREPARATION FOR ORAL USE

This application is a continuation of U.S. application Ser. No. 13/591,902, filed Aug. 22, 2012, which is a continuation of International Application No. PCT/JP2011/053642, filed on Feb. 21, 2011, entitled "SUSTAINED-RELEASE SOLID PREPARATION FOR ORAL USE", which claims the benefit of Japanese Patent Application Number JP 2010-035882, filed on Feb. 22, 2010, all of which are hereby incorporated by reference in their entireties.

FIELD OF THE INVENTION

The present invention relates to a sustained-release matrix preparation that reliably exhibits its main pharmacological effect when orally administered once or twice a day.

BACKGROUND

Sustained-release preparations for the adjustment of blood concentrations of drugs are highly useful in terms of separation between the main pharmacological effect and adverse reaction, improvement in compliance (e.g., the number of doses reduced by improvement in prolonged efficacy), medical economy, etc. In this regard, some techniques have been reported for sustained-release preparations. Meanwhile, since compounds exhibiting the main pharmacological effect have diverse chemical properties, some sustained release techniques, albeit still insufficient, adaptable to the diverse chemical properties of these compounds have been reported (see e.g., Patent Documents 1 and 2).

The properties of a drug itself can be classified broadly into neutral, acidic, and basic properties. Among others, solubility (degree of solubility) in water differs greatly between compounds. Low water-soluble compounds have many disadvantages in the design of preparations to improve dissolution properties. Acidic drugs refer to acidic compounds that are acidic in the free form (whose acidic group does not constitute a salt such as an alkali- or amine-adduct salt). Acidic drugs are disadvantageously low soluble in acidic solutions, for example, in the upper gastrointestinal tract such as the stomach. A salt (alkali- or amine-adduct salt) of an acidic compound disadvantageously becomes a low soluble free acid in an acidic solution. Alternatively, basic drugs refer to basic compounds that are basic in the free form (whose basic group does not constitute a salt such as an acid-adduct salt) and are known to exhibit favorable solubility in strongly acidic aqueous solutions, but exhibit reduced solubility in neutral aqueous solutions such as a neutral buffer. Specifically, basic drugs, when orally administered, exhibit favorable solubility in the stomach, which is acidic. Their solubility, however, is greatly reduced in the lower gastrointestinal tract such as the large intestine, which is neutral with little water, probably leading to a reduced absorption rate of the drug.

For example, a challenge for the design of sustained-release preparations for oral administration containing a basic drug is dose dumping of the drug when the preparation collapses due to mechanical stress resulting from the presence of food in the acidic environment of the upper gastrointestinal tract exhibiting high water-solubility, gastrointestinal motility, and so on. Furthermore, preparation strength may be enhanced by, for example, an increased amount of a sustained-release agent in order to avoid dose dumping of the drug. In such a case, still, the challenge for a sustained-release preparation containing a basic drug whose water solubility is reduced in the neutral region is to improve the dissolution properties of the preparation in the lower gastrointestinal tract and maintain drug absorption. No previous technique for sustained-release preparations containing a basic drug can simultaneously achieve, at satisfactory levels, avoidance of dose dumping of the drug in an acidic environment such as the upper gastrointestinal tract and prolonged dissolution in the lower gastrointestinal tract, which is a neutral environment.

CITATION LIST

Patent Document

Patent Document 1: National Publication of International Patent Application No. 2006/507216
Patent Document 2: National Publication of International Patent Application No. 2004/518676

SUMMARY OF THE INVENTION

Technical Problem

An object of the present invention is to avoid dose dumping of a drug caused by mechanical stress resulting from gastrointestinal motility in the presence of food in the acidic environment of the upper gastrointestinal tract, particularly, the stomach, and to improve the dissolution properties of the drug in the lower gastrointestinal tract, which is the neutral region, and thereby provide a sustained-release preparation for oral administration containing, as a principal pharmaceutically active ingredient, a drug that reliably exhibits its main pharmacological effect when orally administered once or twice a day.

Solution to Problem

As a result of conducting studies on the formulation of sustained-release preparations for oral administration, the present inventors have found that a sustained-release matrix preparation containing a pharmacologically active drug, a pH-dependent polymer base, a hydrophilic gel-forming polymer material, and an excipient can avoid dose dumping of the drug under an acidic environment and can be improved in its dissolution properties in the neutral region. Based on this finding, the present invention has been completed.

Specifically, the present invention provides the following (1) to (54):

(1) A sustained-release matrix preparation obtained by mixing of the following components (A) to (D):
  (A) a pharmacologically active drug;
  (B) a pH-dependent polymer base;
  (C) a hydrophilic gel-forming polymer material; and
  (D) an excipient
followed by molding.

(2) The sustained-release matrix preparation according to (1), wherein, when the preparation is subjected to a dissolution test by the paddle method at rotation rates of 50 rpm and 200 rpm at 37±0.5° C. for 2 hours in 0.01 N hydrochloric acid (900 mL), the preparation exhibits a difference in average percentage dissolution (value at the rotation rate of 200 rpm in the paddle method−value at the rotation rate of 50 rpm in the paddle method) of the pharmacologically active drug in the dissolution test medium of 10% or lower, or exhibits an average percentage dissolution ratio (value at the rotation rate of 200 rpm in the paddle method/value at the rotation rate of 50 rpm in the paddle method) of the pharmacologically active drug in the dissolution test medium of 2.0 or lower.

(3) The sustained-release matrix preparation according to (2), wherein the difference in average percentage dissolution (value at the rotation rate of 200 rpm in the paddle method−value at the rotation rate of 50 rpm in the paddle method) of the pharmacologically active drug in the dissolution test medium is 5% or lower.

(4) The sustained-release matrix preparation according to (2) or (3), wherein the average percentage dissolution ratio (value at the rotation rate of 200 rpm in the paddle method/value at the rotation rate of 50 rpm in the paddle method) of the pharmacologically active drug in the dissolution test medium is 1.5 or lower.

(5) The sustained-release matrix preparation according to any one of (1) to (4), wherein the pH-dependent polymer base (B) is an enteric coating base.

(6) The sustained-release matrix preparation according to (5), wherein the enteric coating base is hydroxypropyl methylcellulose acetate succinate or a methacrylic acid-methyl methacrylic acid copolymer.

(7) The sustained-release matrix preparation according to (5), wherein the enteric coating base is hydroxypropyl methylcellulose acetate succinate.

(8) The sustained-release matrix preparation according to any one of (1) to (7), wherein the pH-dependent polymer base (B) has an average particle size $D_{50}$ of 40 μm or smaller.

(9) The sustained-release matrix preparation according to any one of (1) to (7), wherein the pH-dependent polymer base (B) has an average particle size $D_{50}$ of 20 μm or smaller.

(10) The sustained-release matrix preparation according to any one of (1) to (7), wherein the pH-dependent polymer base (B) has an average particle size $D_{50}$ of 10 μm or smaller.

(11) The sustained-release matrix preparation according to any one of (1) to (10), wherein the content of the pH-dependent polymer base (B) is in the range of 10 to 95% by weight with respect to the total amount of the preparation.

(12) The sustained-release matrix preparation according to any one of (1) to (10), wherein the content of the pH-dependent polymer base (B) is in the range of 15 to 80% by weight with respect to the total amount of the preparation.

(13) The sustained-release matrix preparation according to any one of (1) to (10), wherein the content of the pH-dependent polymer base (B) is in the range of 20 to 50% by weight with respect to the total amount of the preparation.

(14) The sustained-release matrix preparation according to any one of (1) to (13), wherein the hydrophilic gel-forming polymer material (C) is a cellulose derivative.

(15) The sustained-release matrix preparation according to (14), wherein the cellulose derivative is hydroxypropyl methylcellulose or hydroxypropyl cellulose.

(16) The sustained-release matrix preparation according to any one of (1) to (15), wherein the excipient (D) is a water-soluble excipient.

(17) The sustained-release matrix preparation according to (16), wherein the water-soluble excipient is a saccharide or a nonionic water-soluble polymer.

(18) The sustained-release matrix preparation according to (17), wherein the nonionic water-soluble polymer is polyvinylpyrrolidone.

(19) The sustained-release matrix preparation according to (17), wherein the saccharide is lactose or a sugar alcohol.

(20) The sustained-release matrix preparation according to (17), wherein the saccharide is a sugar alcohol.

(21) The sustained-release matrix preparation according to (19) or (20), wherein the sugar alcohol is mannitol, xylitol, or erythritol.

(22) The sustained-release matrix preparation according to any one of (1) to (21), further containing an organic acid.

(23) The sustained-release matrix preparation according to (22), wherein the organic acid is fumaric acid or alginic acid.

(24) The sustained-release matrix preparation according to (22), wherein the organic acid is fumaric acid.

(25) The sustained-release matrix preparation according to any one of (1) to (24), wherein the pharmacologically active drug (A) exhibits the following degree of solubility:
(degree of solubility in the neutral state)/(degree of solubility in the acidic state) in the range of 0.00001 to 0.6.

(26) The sustained-release matrix preparation according to any one of (1) to (24), wherein the pharmacologically active drug (A) exhibits the following degree of solubility:
(degree of solubility in the neutral state)/(degree of solubility in the acidic state) in the range of 0.001 to 0.5.

(27) The sustained-release matrix preparation according to any one of (1) to (24), wherein the pharmacologically active drug (A) exhibits the following degree of solubility:
the lowest degree of solubility in the neutral state (in the range of 7.5>pH>5) of 3 mg/ml or lower.

(28) The sustained-release matrix preparation according to any one of (1) to (24), wherein the pharmacologically active drug (A) exhibits the following degree of solubility:
the lowest degree of solubility in the neutral state (in the range of 7.5>pH>5) of 0.5 mg/ml or lower.

(29) The sustained-release matrix preparation according to any one of (1) to (28), wherein the pharmacologically active drug (A) is a basic drug.

(30) The sustained-release matrix preparation according to any one of (1) to (24), wherein the pharmacologically active drug (A) is a compound selected from the group consisting of the following:
(±)-1-(carbazol-4-yloxy)-3-[[2-(o-methoxyphenoxy)ethyl]amino]-2-propanol;
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide; and
$N^1$-(5-chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-([1,3,4]oxadiazol-2-yl)cyclohexyl]ethanediamide
or a pharmacologically acceptable salt thereof, or a hydrate thereof.

(31) The sustained-release matrix preparation according to any one of (1) to (30), wherein the preparation is a tablet or granules.

(32) A sustained-release preparation obtained by mixing of
(A) a pharmacologically active drug,
(B) hydroxypropyl methylcellulose acetate succinate having a median size ($D_{50}$) of 40 μm or smaller,
(C) a cellulose derivative, and
(D) a saccharide or a nonionic water-soluble polymer followed by molding.

(33) The preparation according to (32), wherein the component (B) has a median size ($D_{50}$) of 20 μm or smaller.

(34) The preparation according to (32), wherein the component (B) has a median size ($D_{50}$) of 10 μm or smaller.

(35) The preparation according to (32), wherein the component (B) has a median size ($D_{50}$) of 10 μm or smaller and $D_{90}$ of 20 μm or smaller.

(36) The preparation according to any one of (32) to (35), wherein the content of the component (B) in the preparation is 15 to 80% by weight.
(37) The preparation according to any one of (32) to (35), wherein the content of the component (B) in the preparation is 20 to 50% by weight.
(38) The preparation according to any one of (32) to (35), wherein the content of the component (B) in the preparation is 25 to 45% by weight.
(39) The preparation according to any one of (32) to (38), wherein the content of the component (A) in the preparation is 2 to 35% by weight.
(40) The preparation according to any one of (32) to (39), wherein the cellulose derivative as the component (C) in the preparation is hydroxypropyl cellulose.
(41) The preparation according to (40), wherein the hydroxypropyl cellulose is hydroxypropyl cellulose having a 100-mesh sieve passing rate of 99%.
(42) The preparation according to (40) or (41), wherein the hydroxypropyl cellulose is hydroxypropyl cellulose having a viscosity of 150 to 400 mPa·s or 1000 to 4000 mPa·s.
(43) The preparation according to any one of (32) to (42), wherein the content of the component (C) in the preparation is 5 to 35% by weight.
(44) The preparation according to any one of (32) to (43), wherein the component (D) in the preparation is a saccharide.
(45) The preparation according to (44), wherein the saccharide is lactose or a sugar alcohol.
(46) The preparation according to (45), wherein the sugar alcohol is mannitol, xylitol, or erythritol.
(47) The preparation according to any one of (32) to (43), wherein the component (D) in the preparation is a nonionic water-soluble polymer.
(48) The preparation according to (47), wherein the nonionic water-soluble polymer is povidone.
(49) The preparation according to any one of (32) to (48), further containing an organic acid.
(50) The preparation according to (49), wherein the organic acid is fumaric acid or alginic acid.
(51) The preparation according to (49), wherein the organic acid is fumaric acid.
(52) The preparation according to any one of (32) to (51), wherein the component (A) is a basic drug.
(53) The preparation according to any one of (32) to (51), wherein the component (A) is a compound selected from the group consisting of
(±)-1-(carbazol-4-yloxy)-3-[[2-(o-methoxyphenoxy)ethyl]amino]-2-propanol,
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide, and
$N^1$-(5-chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-([1,3,4]oxadiazol-2-yl)cyclohexyl]ethanediamide
or a pharmacologically acceptable salt thereof, or a hydrate thereof.
(54) The preparation according to any one of (32) to (53), wherein the dosage form of the preparation is a tablet.

Advantageous Effects of the Invention

The present invention can provide a sustained-release pharmaceutical composition for oral administration containing a pharmacologically active drug. Thus, the present invention provides, for example, an oral matrix preparation having a prolonged effect, which contains activated blood coagulation factor X (FXa) inhibitor compound (1) as a pharmaceutically active ingredient. The sustained-release pharmaceutical composition of the present invention has a favorable tablet strength that prevents dose dumping in an acidic solution, and has favorable dissolution properties in a neutral solution. Thus, the sustained-release pharmaceutical composition of the present invention is effective for maintaining a prolonged dissolution of the pharmacologically active drug contained therein from the duodenum through the small intestine to the lower gastrointestinal tract.

BRIEF DESCRIPTION OF THE DRAWINGS

FIG. 2 is a diagram showing dissolution properties in an acidic solution (the paddle method, dissolution test medium: 0.01 N hydrochloric acid (900 mL), paddle rotation rate: 50 rpm and 200 rpm) for tablets having formulation 1a.
FIG. 4 is a diagram showing dissolution properties in a neutral solution (the paddle method, 900 mL, 50 rpm; dissolution test medium: phosphate buffer, pH 6.8) for tablets having formulation 1a.
FIG. 5 is a diagram showing dissolution properties in an acidic solution (the paddle method, dissolution test medium: 0.01 N hydrochloric acid (900 mL), paddle rotation rate: 50 rpm and 200 rpm) for tablets having formulation 2a.
FIG. 6 is a diagram showing dissolution properties in a neutral solution (the paddle method, 900 mL, 50 rpm; dissolution test medium: phosphate buffer, pH 6.8) for tablets having formulations 1 and 3a.
FIG. 7 is a diagram showing dissolution properties in an acidic solution (the paddle method, dissolution test medium: 0.01 N hydrochloric acid (900 mL), paddle rotation rate: 50 rpm and 200 rpm) for tablets having formulations 1, 4a, and 5a.
FIG. 8 is a diagram showing dissolution properties in a neutral solution (the paddle method, 900 mL, 50 rpm; dissolution test medium: phosphate buffer, pH 6.8) for tablets having formulations 1, 4a, and 5a.
FIG. 10 is a diagram showing dissolution properties in an acidic solution (the paddle method, dissolution test medium: 0.01 N hydrochloric acid (900 mL), paddle rotation rate: 50 rpm and 200 rpm) for tablets having formulation 6a.
FIG. 12 is a diagram showing dissolution properties in a neutral solution (the paddle method, 900 mL, 50 rpm; dissolution test medium: phosphate buffer, pH 6.8) for tablets having formulation 6a.

0.01 N hydrochloric acid (900 mL), paddle rotation rate: 50 rpm and 200 rpm) for tablets having formulation 7a.

Figure 14:
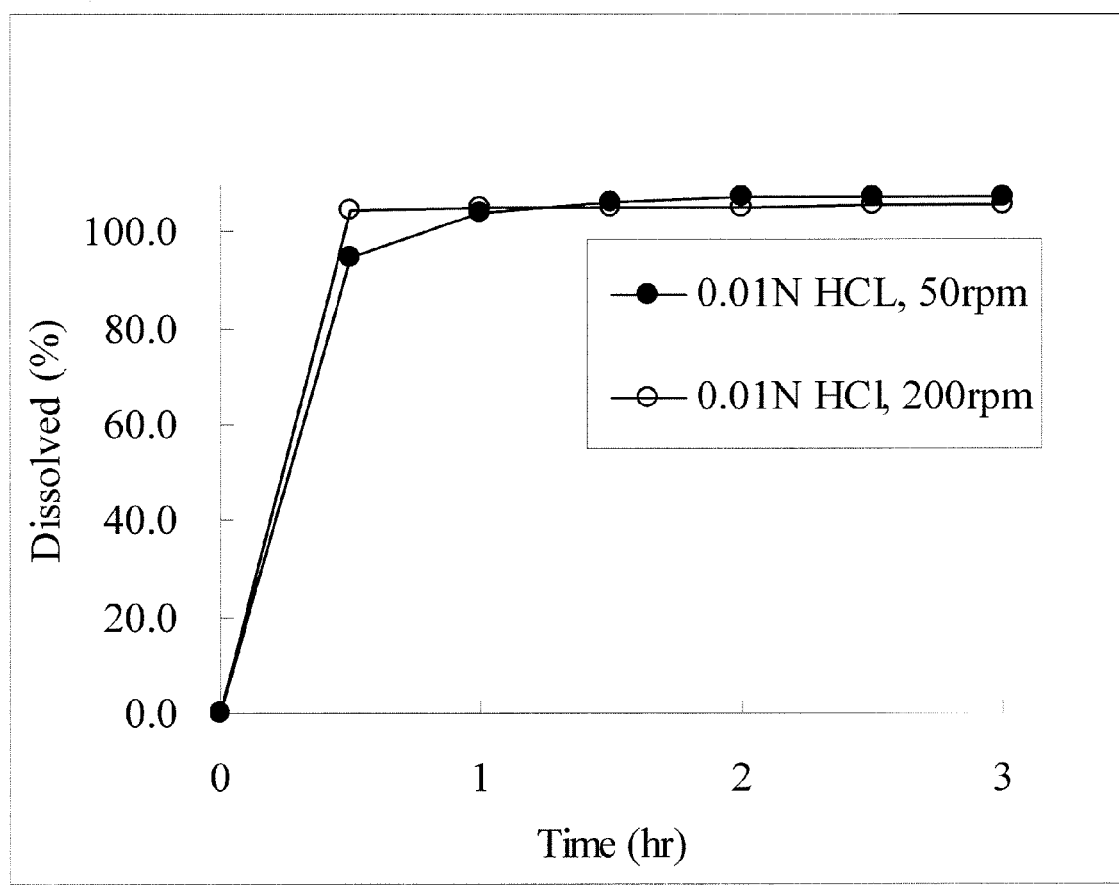

FIG. 14 is a diagram showing dissolution properties in an acidic solution (the paddle method, dissolution test medium: 0.01 N hydrochloric acid (900 mL), paddle rotation rate: 50 rpm and 200 rpm) for tablets having formulation 8a.

Figure 15:
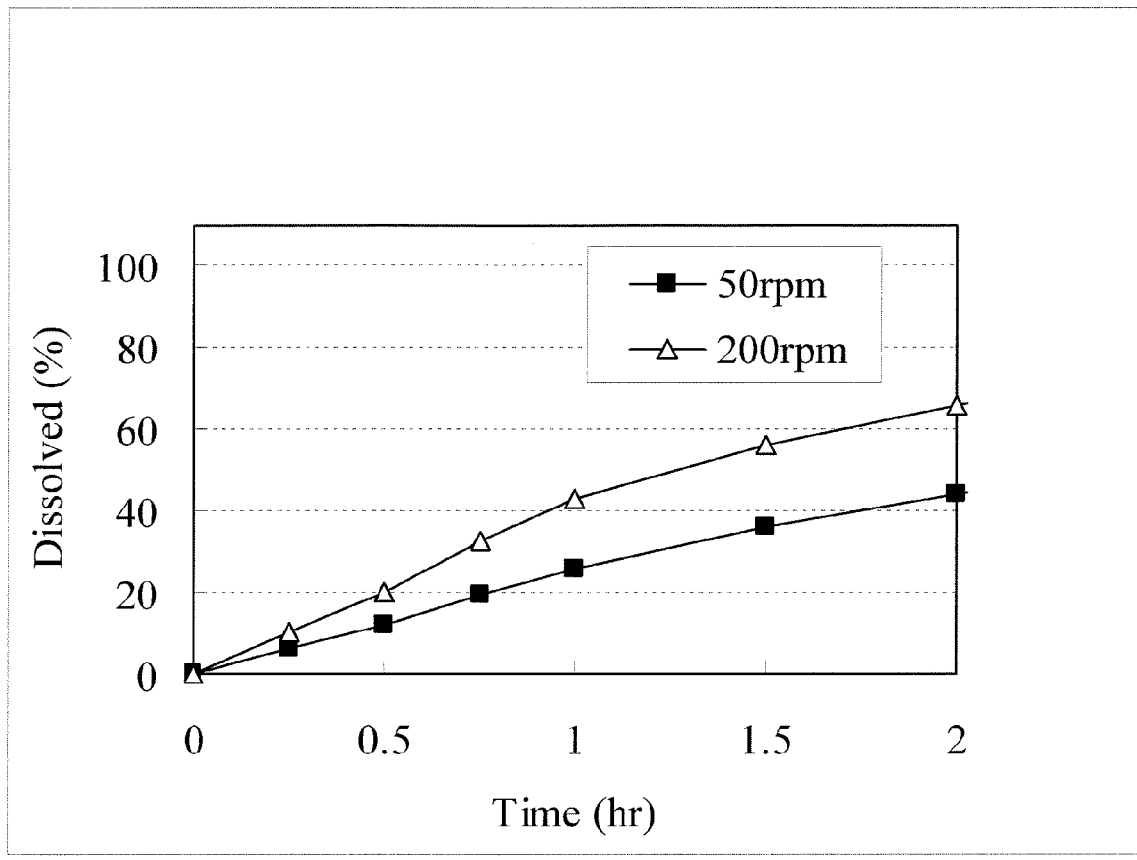

FIG. 15 is a diagram showing dissolution properties in an acidic solution (the paddle method, dissolution test medium: 0.01 N hydrochloric acid (900 mL), paddle rotation rate: 50 rpm and 200 rpm) for tablets having formulation 9a.

Figure 16:
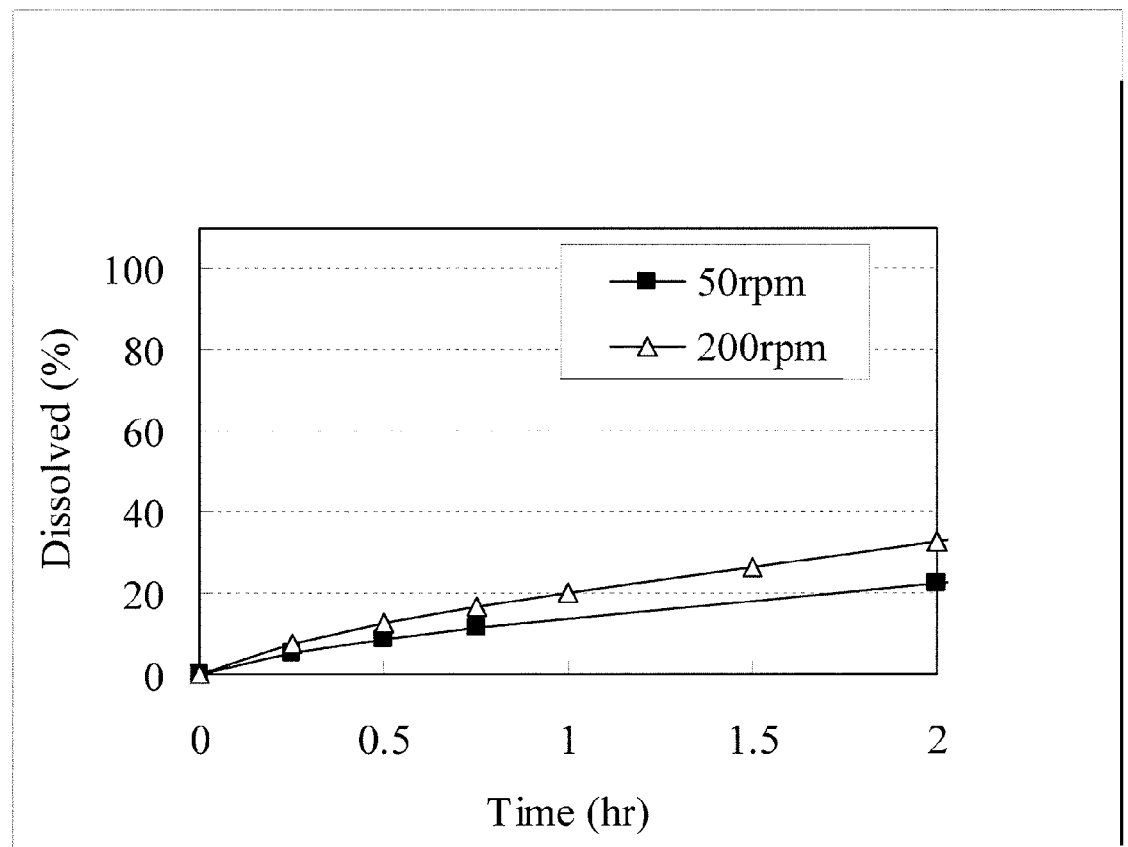

FIG. 16 is a diagram showing dissolution properties in an acidic solution (the paddle method, dissolution test medium: 0.01 N hydrochloric acid (900 mL), paddle rotation rate: 50 rpm and 200 rpm) for tablets having formulation 9b.

Figure 17:
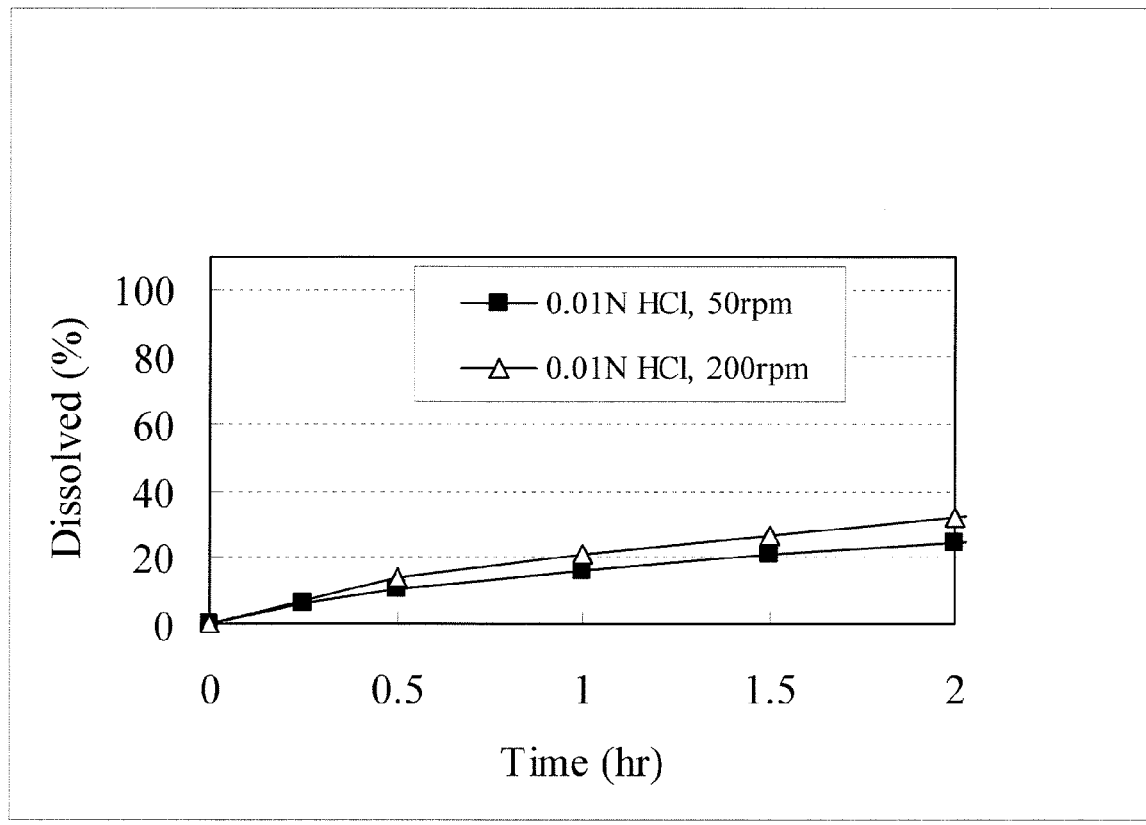

FIG. 17 is a diagram showing dissolution properties in an acidic solution (the paddle method, dissolution test medium: 0.01 N hydrochloric acid (900 mL), paddle rotation rate: 50 rpm and 200 rpm) for tablets having formulation 9c.

Figure 18:
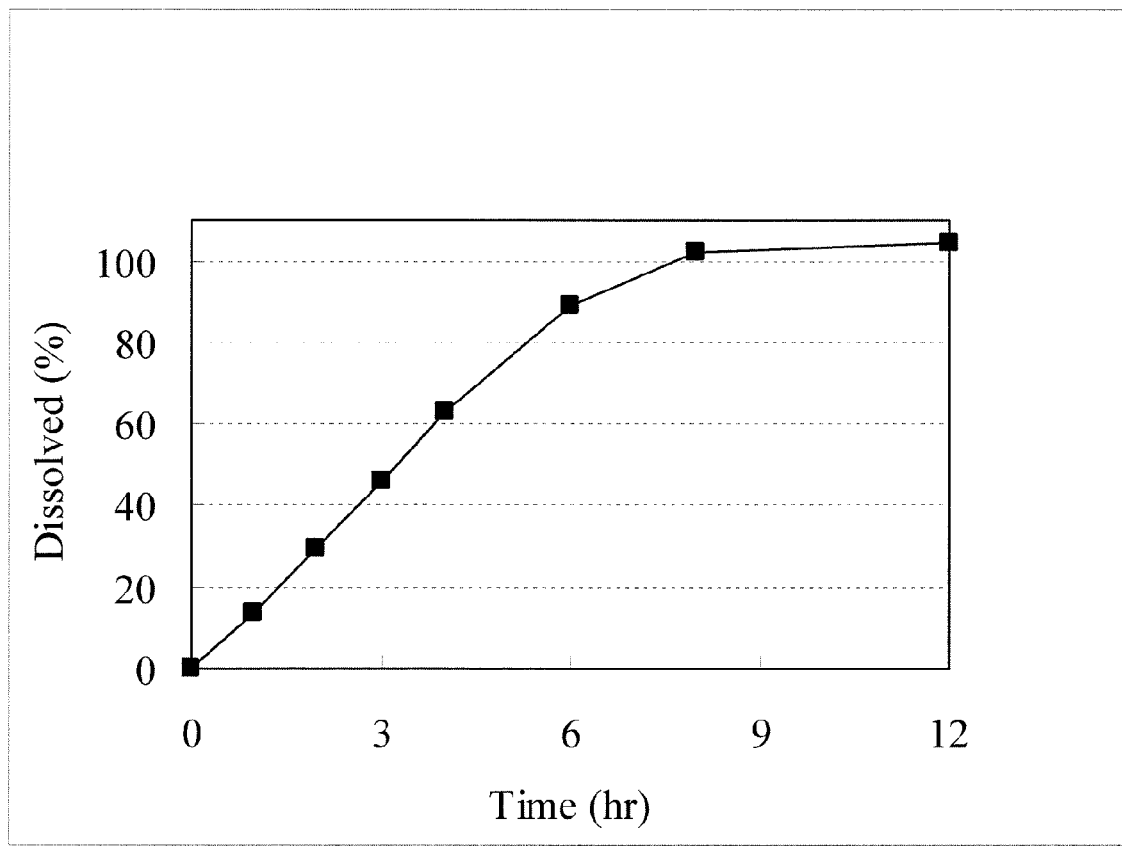

FIG. 18 is a diagram showing dissolution properties in a neutral solution (the paddle method, 900 mL, 50 rpm; dissolution test medium: phosphate buffer, pH 6.8) for tablets having formulation 9a.

Figure 19:
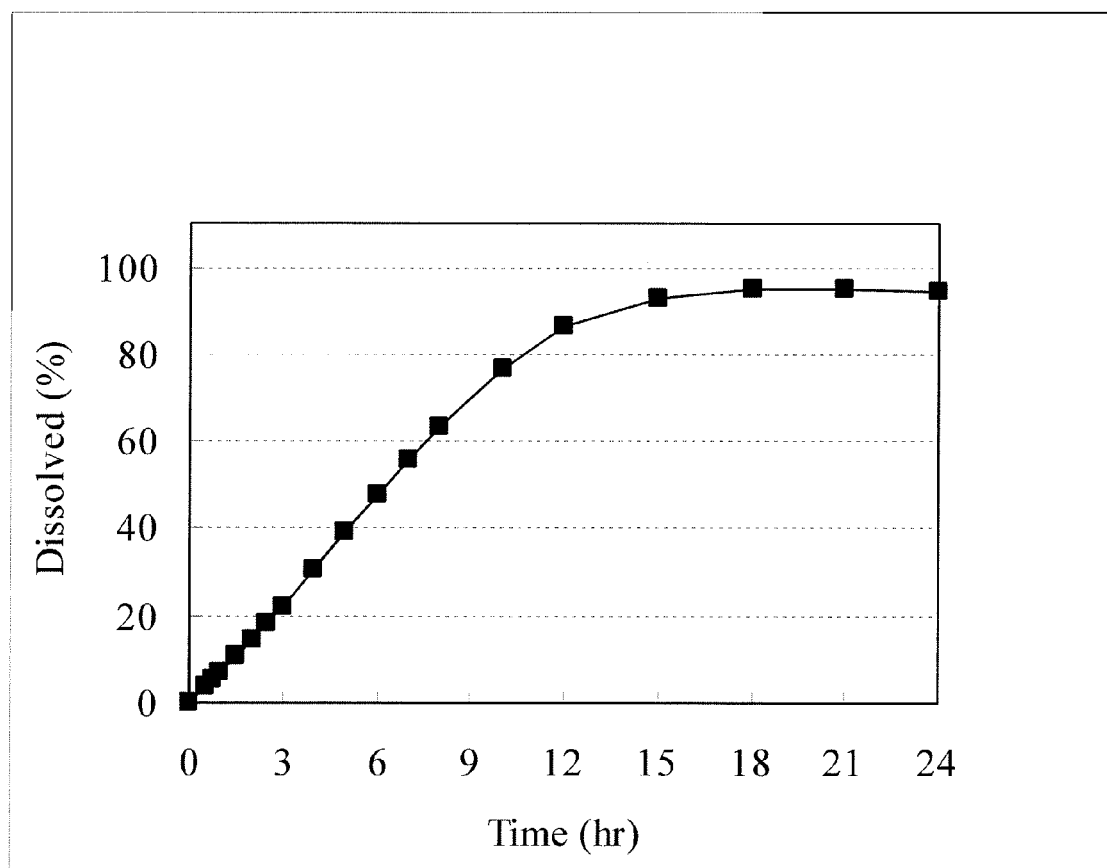

FIG. 19 is a diagram showing dissolution properties in a neutral solution (the paddle method, 900 mL, 50 rpm; dissolution test medium: phosphate buffer, pH 6.8) for tablets having formulation 9b.

Figure 20:
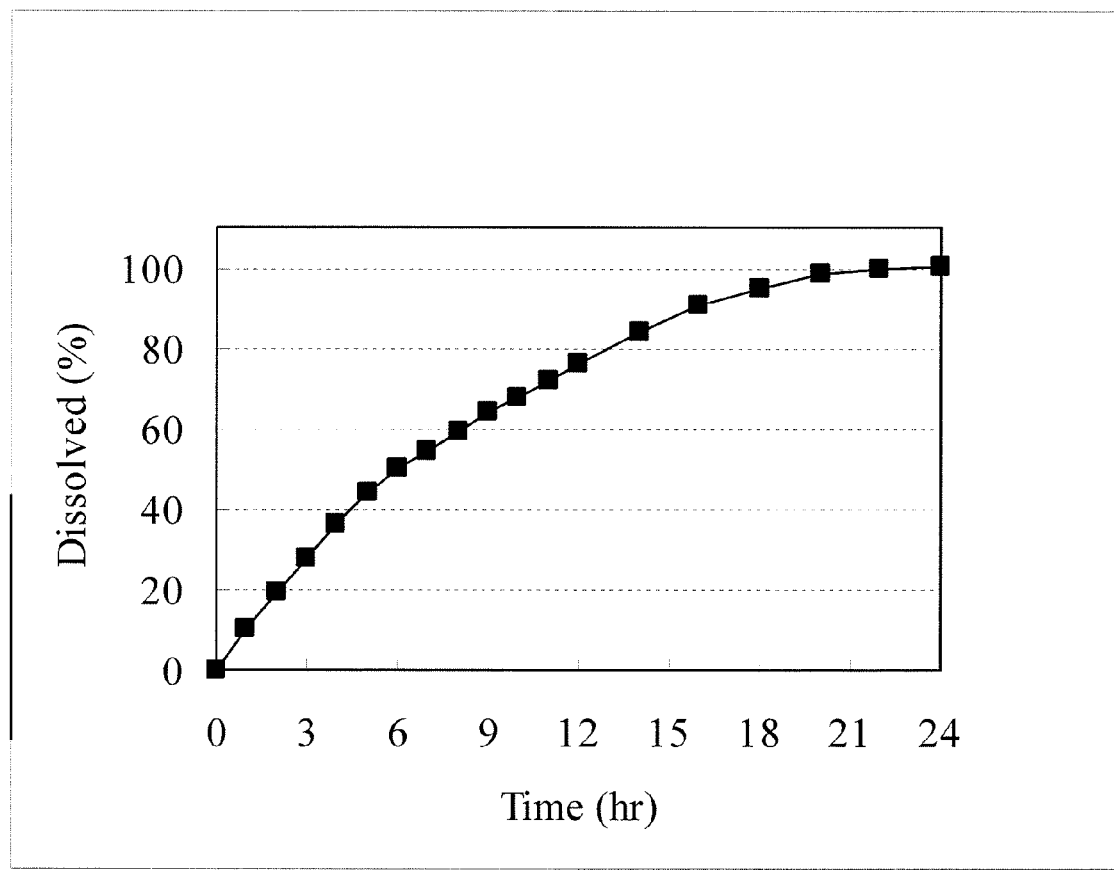

FIG. 20 is a diagram showing dissolution properties in a neutral solution (the paddle method, 900 mL, 50 rpm; dissolution test medium: phosphate buffer, pH 6.8) for tablets having formulation 9c.

Figure 21:
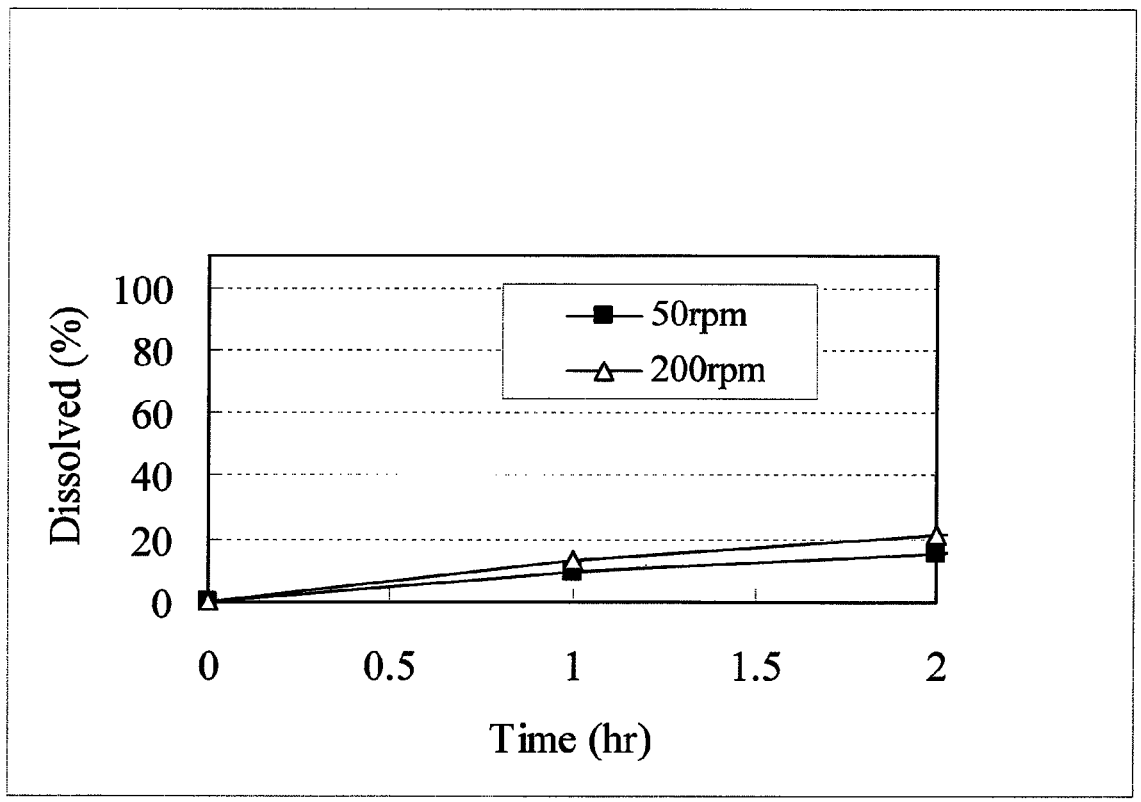

FIG. 21 is a diagram showing dissolution properties in an acidic solution [the paddle method; dissolution test medium: the JP 1st dissolution test fluid (JP1) (900 mL) described in the Japanese Pharmacopoeia, paddle rotation rate: 50 rpm and 200 rpm] for tablets having formulation 10.

Figure 22:
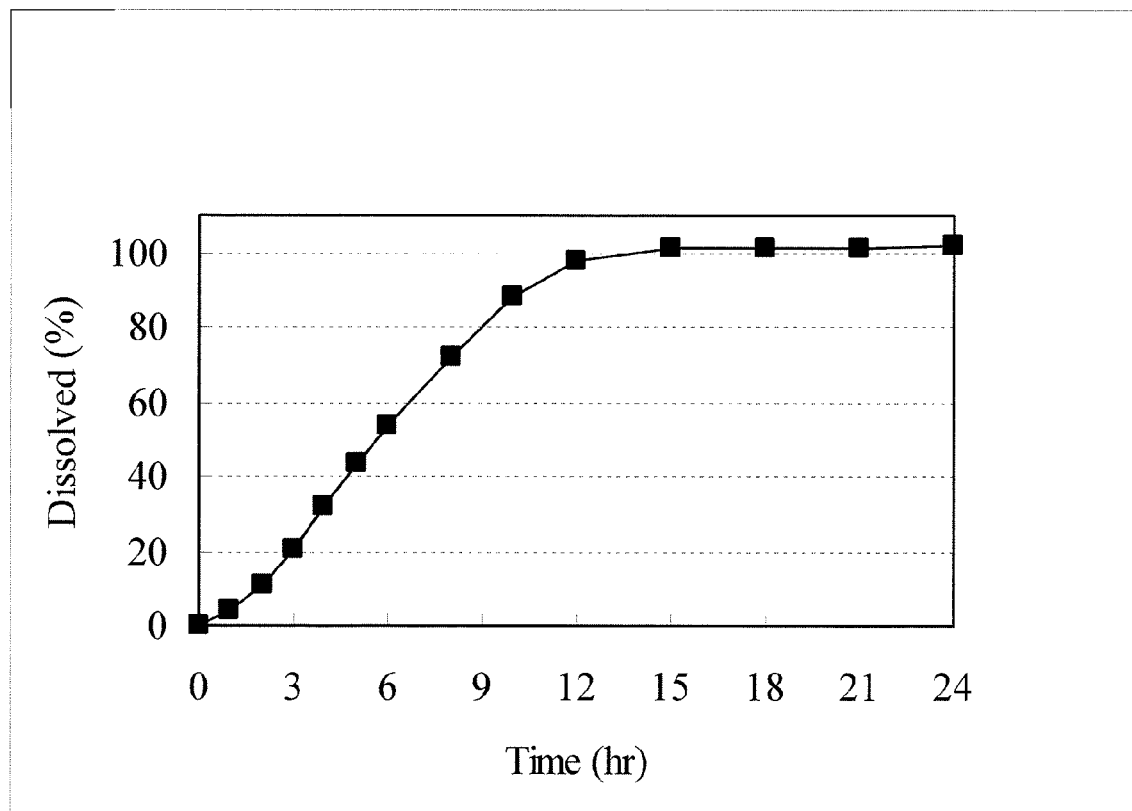

FIG. 22 is a diagram showing dissolution properties in a neutral solution [the paddle method, 900 mL, 50 rpm; dissolution test medium: the JP 2nd dissolution test fluid (JP2) described in the Japanese Pharmacopoeia] for tablets having formulation 10.

Figure 23:
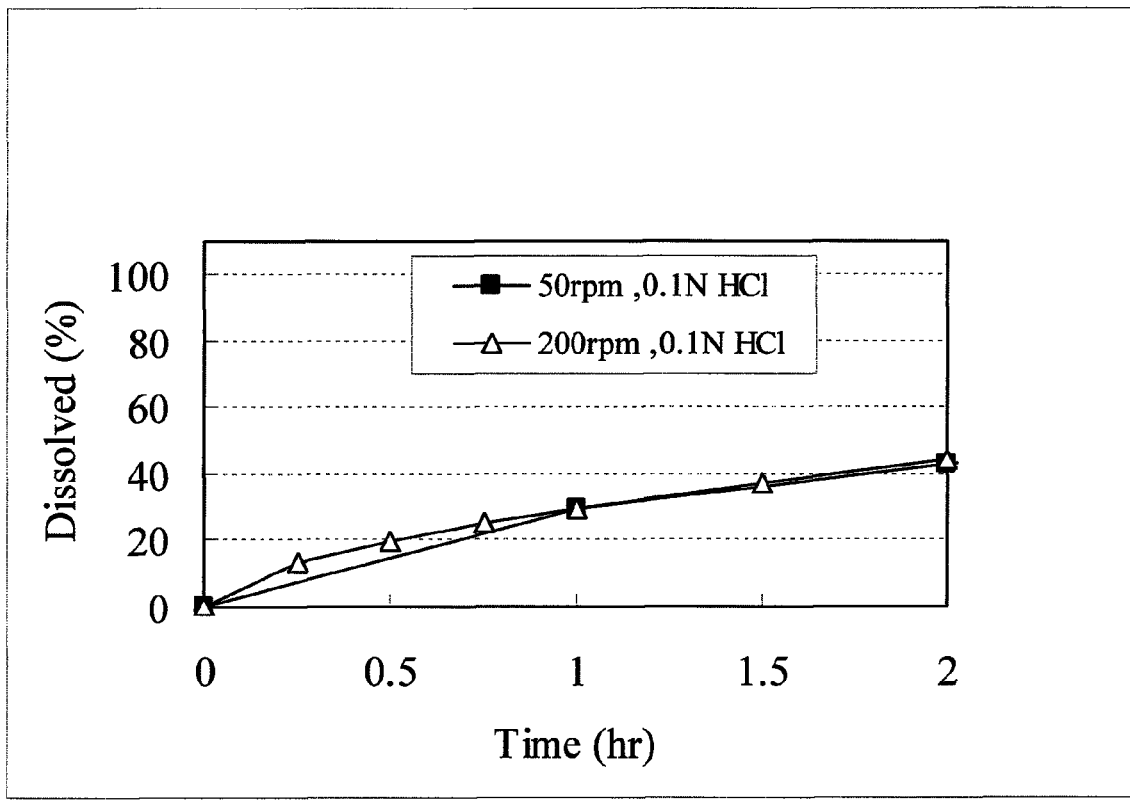

FIG. 23 is a diagram showing dissolution properties in an acidic solution [the paddle method; dissolution test medium: the JP 1st dissolution test fluid (JP1) (900 mL) described in the Japanese Pharmacopoeia, paddle rotation rate: 50 rpm and 200 rpm] for tablets having formulation 11a.

DETAILED DESCRIPTION

Hereinafter, the present invention will be described in detail.

In the present specification, "acidic solution" means an acidic dissolution test medium used for evaluation of dissolution properties in the upper gastrointestinal tract such as the stomach. Non-limiting examples of the acidic dissolution test medium can include: the JP 1st dissolution test fluid described in the Japanese Pharmacopoeia; and USP 0.1 N hydrochloric acid, 0.01 N hydrochloric acid, and Simulated Gastric Fluid without Enzyme described in the United States Pharmacopoeia.

In the present specification, "neutral solution" means a neutral dissolution test medium used for evaluation of drug dissolution properties in the small intestine, the large intestine, or the like. Non-limiting examples of the neutral dissolution test medium can include dissolution test media (pH 6.8) such as: the JP 2nd dissolution test fluid and phosphate buffer (pH 6.8) described in the Japanese Pharmacopoeia; USP Phosphate Buffer (pH 6.8) and Simulated Intestinal Fluid without Enzyme described in the United States Pharmacopoeia; and Phosphate Buffer Solution (pH 6.8) described in the European Pharmacopoeia.

The aforementioned dissolution test medium is prepared through methods described in the corresponding pharmacopoeia or the like of each country. When the employed dissolution test medium is a buffer solution, variation of the pH of the test medium is preferably within ±0.05 of the pH defined for each dissolution medium.

Examples of the paddle method using an acidic dissolution medium for the evaluation of dissolution properties of the sustained-release matrix preparation of the present invention in the upper gastrointestinal tract can include a method in which a dissolution test is conducted by the paddle method at rotation rates of 50 rpm and 200 rpm at 37±0.5° C. for 2 hours in 0.01 N hydrochloric acid (900 mL). As described above, when the pharmacologically active drug in the preparation is a basic drug, dose dumping of the drug becomes a problem because the preparation collapses due to mechanical stress resulting from the presence of food in the acidic environment of the upper gastrointestinal tract exhibiting high water-solubility, gastrointestinal motility, and so on. Thus, the average percentage dissolution of the pharmacologically active drug in the dissolution test medium is preferably a value that allows preparation strength to be maintained and the dissolution rate to be kept within a predetermined range at the rotation rates of 200 rpm and/or 50 rpm in the paddle method. The average percentage dissolution of the pharmacologically active drug in the dissolution test medium after 2 hours is preferably 50% or lower, more preferably 40% or lower, even more preferably 30% or lower, at the rotation rates of 200 rpm and/or 50 rpm in the paddle method. Moreover, when the preparation is subjected to the dissolution test method for 2 hours, the difference in average percentage dissolution (value at the rotation rate of 200 rpm in the paddle method–value at the rotation rate of 50 rpm in the paddle method) of the pharmacologically active drug in the dissolution test medium is preferably 25% or lower, more preferably 20% or lower, even more preferably 15% or lower, further preferably 10% or lower, particularly preferably 5% or lower. Moreover, the average percentage dissolution ratio (value at the rotation rate of 200 rpm in the paddle method/value at the rotation rate of 50 rpm in the paddle method) of the pharmacologically active drug in the dissolution test medium after 2 hours is preferably 2.0 or lower, more preferably 1.5 or lower, particularly preferably 1.3 or lower.

Examples of the paddle method using a neutral dissolution medium for the evaluation of dissolution properties of the sustained-release matrix preparation of the present invention in the neutral region can include a method in which a dissolution test is conducted by the paddle method at a rotation rate of 50 rpm at 37±0.5° C. in phosphate buffer (pH 6.8; 900 mL). The average percentage dissolution of the pharmacologically active drug in the dissolution test medium is preferably a dissolution rate exceeding 85% within 24 hours after the start of the dissolution test. Moreover, the sustained-release preparation preferably exhibits an average percentage dissolution of the pharmacologically active drug of 70% or lower in 3 hours after the start of the dissolution test and higher than 85% within 24 hours after the start of the dissolution test, more preferably 50% or lower in 3 hours after the start of the dissolution test and higher than 85% within 24 hours after the start of the dissolution test.

USP Apparatus 3 (Bio-Dis method), which is a dissolution test method under conditions close to the environment of the human gastrointestinal tract, may be used for the dissolution test.

The concentration of the drug in a solution can be measured using conditions (test medium, shaking rate, and measurement time) shown in Examples described later. In the dissolution test, the average percentage dissolution and dissolution time of the pharmacologically active drug in the dissolution test medium can be calculated using the UV method or the like.

As used herein, "average percentage dissolution" refers to the average of percentage dissolution values obtained from at least 2, preferably 6, more preferably 12 solid preparation samples for each type of solid preparation.

Moreover, the dissolution properties of the pharmacologically active drug from the sustained-release matrix preparation of the present invention can be confirmed using an in vivo animal test. Examples of the in vivo animal test can include in vivo absorption property evaluation using dogs. In general, an orally administered preparation allegedly passes through the stomach and the small intestine and then stays for a long time in the large intestine. Therefore, for sustained-release preparations having a long dissolution time, it is very important to prolong drug release in the large intestine in which the preparation stays for a long time. Examples of a method for confirming the absorption properties of the pharmacologically active drug contained in the preparation in the large intestine can include canine large intestinal absorption property evaluation in which the preparation is directly administered into the canine large intestine. Specifically, the absorption properties in the canine large intestine can be confirmed from blood concentrations measured after administration, and evaluated based on the relative bioavailability (BA) or the like of each tablet from their ratios to those of an orally administered aqueous solution of the pharmacologically active drug.

In the present specification, the "pharmacologically active drug" is preferably a relatively low water-soluble drug that exhibits the main pharmacological effect of the formulation of the preparation. A neutral compound of the pharmacologically active drug means a compound that does not have a group dissociable by ionization in the acidic or basic state in its molecule. Moreover, an acidic compound means a drug having an acidic group typified by a carboxy group, a phenolic hydroxy group, a phosphoric acid group, a sulfonic acid group, a tetrazolyl group, or the like. Furthermore, a basic drug means a drug having a basic nitrogen atom typified by an amino group, a piperidinyl group, a piperazinyl group, or the like in its molecule. In the present invention, particularly, a basic drug is preferred. The basic drug has physicochemical properties in which the degree of solubility is lower in the neutral state (7.5>pH>5) in the small intestine or the large intestine than that in the acidic state (pH 2).

As described above, the basic drug refers to a drug having a degree of solubility that is lower in the neutral state than in the acidic state. Non-limiting examples of the rate of this reduction in the degree of solubility in the neutral state can include the following ranges:
preferably, (degree of solubility in the neutral state)/(degree of solubility in the acidic state) in the range of 0.00001 to 0.6;
more preferably, (degree of solubility in the neutral state)/ (degree of solubility in the acidic state) in the range of 0.001 to 0.5; and
even more preferably, (degree of solubility in the neutral state)/(degree of solubility in the acidic state) in the range of 0.01 to 0.1.

In the present specification, the "basic drug" preferably has a degree of solubility in the range of 1 to 500 mg/ml in the acidic region (the JP 1st dissolution test fluid; pH 1.2, 20±5° C.) and a degree of solubility in the range of 0.01 to 3000 μg/ml in the neutral region (the JP 2nd dissolution test fluid; pH 6.8, 20±5° C.)

More preferred is a basic drug having a degree of solubility in the range of 1 to 500 mg/ml in the acidic region (the JP 1st dissolution test fluid; pH 1.2, 20±5° C.) and a degree of solubility in the range of 10 to 500 μg/ml in the neutral region (the JP 2nd dissolution test fluid; pH 6.8, 20±5° C.). Moreover, the absolute value of the degree of solubility in the drug is preferably the lowest degree of solubility reduced to 3 mg/ml or lower, more preferably 1 mg/ml or lower, even more preferably 0.5 mg/ml or lower, in the neutral state (in the range of 7.5>pH>5).

Specific examples of the "pharmacologically active drug" can include anticoagulant agents shown below.

The anticoagulant agent is preferably an activated blood coagulation factor X (FXa) inhibitor. Specific examples of the FXa inhibitor can include the following (a) to (1):

(a) Darexaban Maleate (tanexaban) (N-[2-hydroxy-6-(4-methoxybenzamido]phenyl)-4-(4-methyl-1,4-diazepan-1-yl)benzamide) [See PFSB/ELD No. 1111-1 (Nov. 11, 2010); Pre-publication copy, Proposed INN: List 101; Research and development pipeline. Yamanouchi Pharmaceutical Co Ltd. Company World Wide Web site, 11 Feb. 2004];

(b) rivaroxaban (5-chloro-N-({(5S)-2-oxo-3-[4-(3-oxo-4-morpholinyl)phenyl]-1,3-oxazolidin-5-yl}methyl)-2-thiophenecarboxamide) [See WFO Drug Information, Vol. 18, No. 3, 2004, page 260; Susanne R, et al, J. Med. Chem., 2005, 48, 5900-5908; D. Kubitza et al, Multiple dose escalation study investigating the pharmacodynamics, safety, and pharmacokinetic of Bay59-7939, an oral, direct Factor Xa inhibitor, in healthy male subjects. Blood, 2003, 102; Abstract 3004];

(c) apixaban (1-(4-methoxyphenyl)-7-oxo-6-[4-(2-oxopiperidin-1-yl)phenyl]-4,5,6,7-tetrahydro-1H-pyrazolo[3,4-c] pyridine-3-carboxamide) [See WFO Drug Information, Vol. 20, No. 1, 2006, page 38; Pinto D J P, Orwat M J, Lam P Y S, et al, Discovery of 1-(4-Methoxyphenyl)-7-oxo-6-(4-(2-oxopiperidin-1-yl)phenyl)-4,5,6,7-tetrahydro-1H-pyrazolo [3,4-c]pyridine-3-carboxamide (Apixaban, BMS-562247), a highly potent, selective, efficacious, and orally bioavailable inhibitor of blood coagulation factor Xa, J. Med. Chem., 50 (22), 5339-56, 2007];

(d) Betrixaban (N-(5-chloropyridin-2-yl)-2-[4-(N,N-dimethylcarbamimidoyl)benzamido]-5-methoxybenzamide) [See WFO Drug Information, Vol. 22, No. 3, 2008, page 226-227; Zhang P, Huang W, Zhu B Y, et al., Discovery of betrixaban (PRT054021), N-(5-chloropyridin-2-yl)-2-(4-(N, N-dimethylcarbamimidoyl)benzamido)-5-methoxybenz-amide, a highly potent, selective, and orally efficacious factor Xa inhibitor, Bioorg Med. Chem. Lett. 19 (8), 2179-85, 2009];

(e) AX-1826, [S. Takehana et al. Japanese Journal of Pharmacology 2000, 82 (Suppl. 1), 213P; T. Kayahara et al. Japanese Journal of Pharmacology 2000, 82 (Suppl. 1), 213P];

(f) HMR-2906, [XVIIth Congress of the International Society for Thrombosis and Haemostasis, Washington D.C., USA, 14-21 Aug. 1999; Generating greater value from our products and pipeline. Aventis SA Company Presentation, 5 Feb. 2004];

(g) Otamixaban (methyl (2R,3R)-2-(3-carbamimidoylbenzyl)-3-[[4-(1-oxidopyridin-4-yl)benzoyl]amino]butanoate) [See WFO Drug Information, Vol. 16, No. 3, 2002, page 257];

(h) BIBT-986 (prodrug: BIBT-1011) [American Chemical Society-226th National Meeting, New York City, N.Y., USA, 2003];

(i) DPC-602, [J. R. Pruitt et al. J. Med. Chem. 2003, 46, 5298-5313];

(j) LY517717 (N-[(1R)-2-[4-(1-methyl-4-piperidinyl)-1-piperazinyl]-2-oxo-1-phenylethyl]-1H-indole-6-carboxamide) [See S. Young, Medicinal Chemistry-12th RSC-SCI Symposium, 7-10 Sep. 2003, Cambridge, UK; M. Wiley et al. 228th ACS National Meeting, Philadelphia, Aug. 22-26, 2004, MEDI-252 & 254];

(k) $N^1$-(5-chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-([1,3,4]oxadiazol-2-yl)cyclohexyl]ethanediamide or a pharmacologically acceptable salt thereof, or a hydrate thereof [see WO 2004/058715]; and (l) $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide or a pharmacologically acceptable salt thereof, or a hydrate thereof [see WO 03/000657; WO 03/000680; and WO 03/016302].

The aforementioned activated blood coagulation factor X (FXa) inhibitor is more preferably a compound represented by the following formula (1) [hereinafter, also abbreviated to compound (1)]:

[Formula 1]

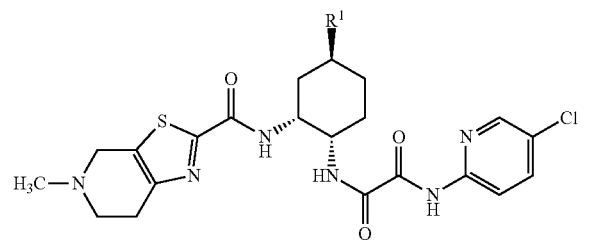

(1)

wherein $R^1$ represents an N,N-dimethylcarbamoyl group or a [1,3,4]oxadiazol-2-yl group.

Compound (1) may be the free form (free base) or a pharmacologically acceptable salt thereof, or a hydrate thereof.

Examples of the salt of the compound represented by formula (1) include hydrochloride, sulfate, hydrobromide, hydroiodide, phosphate, nitrate, benzoate, methanesulfonate, 2-hydroxyethanesulfonate, p-toluenesulfonate, acetate, propionate, oxalate, malonate, succinate, glutarate, adipate, tartrate, maleate, fumarate, malate, and mandelate.

The salt of the compound represented by formula (1) is preferably maleate, hydrochloride, methanesulfonate, or p-toluenesulfonate, particularly preferably maleate or p-toluenesulfonate.

Preferable examples of the compound represented by formula (1) can include the following:

$N^1$-(5-chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-([1,3,4]oxadiazol-2-yl)cyclohexyl]ethanediamide monomaleate;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate; and $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate monohydrate.

Among these preferable compounds, particularly preferred are $N^1$-(5-chloropyridin-2-yl)-$N^2$-[(1S,2R,4S)-2-{[(5-methyl-4,5,6,7-tetrahydrothiazolo[5,4-c]pyridin-2-yl)carbonyl]amino}-4-([1,3,4]oxadiazol-2-yl)cyclohexyl]ethanediamide monomaleate (1a); and $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate monohydrate (1b)

represented by the following formula (1a) [hereinafter, also abbreviated to compound (1a)] and formula (1b) [hereinafter, also abbreviated to compound (1b)], respectively:

[Formula 2]

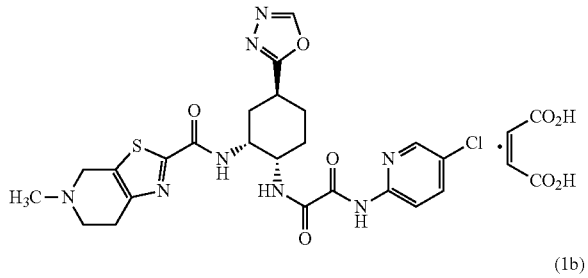

(1a)

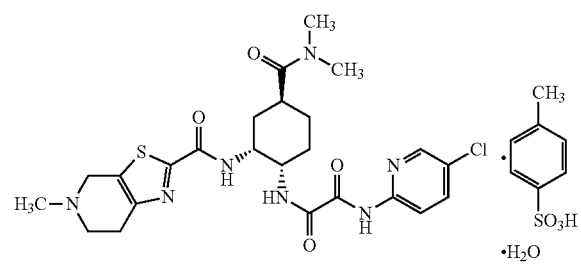

(1b)

These compounds (1) can be produced by a method described in documents or a method equivalent thereto (WO 2003-000657; WO 2003-000680; WO 2003-016302; and WO 2004-058715).

The free base (free form) of compound (1) means the salt (acid-adduct salt) and/or the hydrate formed with compound (1) except for "acid" in the acid-adduct salt or "water" in the hydrate. For example, the free bases (free forms) of compound (1a) and compound (1b) mean $N^1$-(5-chloropyridin-2-yl)- $N^2$-[(1S,2R,4S)-2-{[(5-methyl-4,5,6,7-tetrahydrothiazolo[5,4-c]pyridin-2-yl)carbonyl]amino}-4-([1,3,4]oxadiazol-2-yl)cyclohexyl]ethanediamide (1a-1) and N$^1$-(5-chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (1b-1) represented by the following formula (1a-1) and formula (1b-1), respectively:

[Formula 3]

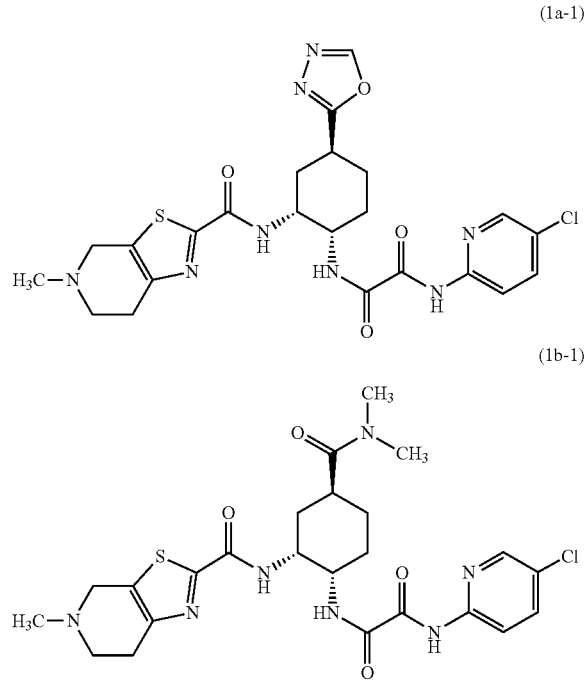

Moreover, preferable examples of the pharmacologically active drug (A) of the present invention can include (±)-1-(carbazol-4-yloxy)-3-[[2-(o-methoxyphenoxy)ethyl]amino]-2-propanol (3) (CAS No.: 72956-09-3) represented by the following formula (2) [hereinafter, also abbreviated to compound (2)]:

[Formula 4]

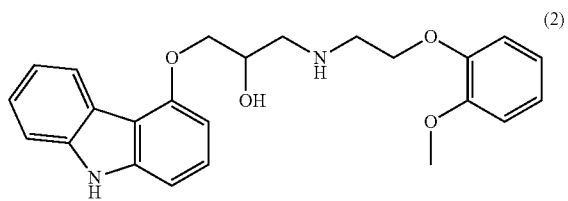

or a pharmacologically acceptable salt thereof, or a hydrate thereof.

Examples of the "pH-dependent polymer base (B)" according to the present invention can include polymer bases that exhibit pH-dependent dissolution properties used in the pharmaceutical field. The "pH-dependent polymer base" can further encompass enteric coating bases and gastric soluble bases. An enteric coating base is preferred. The preferred enteric coating base is hardly soluble under a pH environment such as the stomach and is gradually dissolved under a neutral pH environment such as the small intestine or the large intestine, which is the main absorption site.

Specific examples of the pH-dependent polymer base can include the following (1) to (3):
(1) methacrylic acid copolymers, wherein the methacrylic acid copolymers mean copolymers of two or more monomer species selected from the group consisting of methacrylic acid, methacrylic acid ester, acrylic acid, and acrylic acid ester and are not limited by the combination of the monomers, the number of the monomers used, etc.;
(2) hydroxypropyl methylcellulose acetate succinate (HPMCAS); and
(3) carboxymethylethyl cellulose.

The "pH-dependent polymer base (B)" of the present invention is preferably the methacrylic acid copolymer (1) and HPMCAS (2) described above, more preferably HPMCAS (2).

The methacrylic acid copolymer (1) is preferably a methacrylic acid-methyl methacrylic acid copolymer, a (ethyl acrylate-methyl methacrylate-trimethylammonium ethyl methacrylate chloride) copolymer, a (methacrylic acid-ethyl acrylate) copolymer, a (methacrylic acid-methyl methacrylate) copolymer, more preferably a methacrylic acid-methyl methacrylic acid copolymer. Specific examples of the methacrylic acid-methyl methacrylic acid copolymer can preferably include EUDRAGIT, which is commercially available as EUDRAGIT L100-55 and EUDRAGIT L100.

HPMCAS (2) can be purchased from Shin-Etsu Chemical Co., Ltd. as AQOAT (trade name). The available grades of HPMCAS are LF, MF, HF, LG, MG, and HG, and the like and the HPMCAS is preferably LF grade.

Moreover, preferable examples of the particle size of HPMCAS as the pH-dependent polymer base (B) of the present invention can include 40 μm or smaller, more preferably 20 μm or smaller, even more preferably 10 μm or smaller, particularly preferably 5 μm or smaller, in terms of its average particle size (median size) $D_{50}$. More specifically, the particle size of HPMCAS is preferably $D_{50}$ of 40 μm or smaller, more preferably 20 μm or smaller, even more preferably 10 μm or smaller, particularly preferably 5 μm or smaller. Moreover, its 90% cumulative particle size $D_{90}$ in which the cumulative fraction of the particles is 90% is preferably 20 μm or smaller, more preferably 11 μm or smaller. When HPMCAS is used, the amount of HPMCAS added can be 10 to 95% by weight of the pharmaceutical composition formulation and is more preferably 15 to 80% by weight of the pharmaceutical composition formulation, even more preferably 20 to 50% by weight of the pharmaceutical composition formulation.

The "hydrophilic gel-forming polymer material (C)" according to the present invention is preferably a cellulose derivative. Examples of the cellulose derivative can include hydroxypropyl methylcellulose (HPMC: hypromellose), hydroxypropyl cellulose (HPC), ethyl cellulose, and methyl cellulose. Hypromellose and hydroxypropyl cellulose are preferred, with HPC being more preferred.

Commercially available HPC can be used. According to, for example, the catalog of Nippon Soda Co., Ltd., two types differing in particle size can be obtained: a regular powder grade (40-mesh sieve passing rate of 99%, average particle size: 350 microns) and a fine powder grade (100-mesh sieve passing rate of 99%, average particle size: 150 microns). The regular powder grade is suitable for wet granulation, while the fine powder grade is suitable for direct compression or dry granulation. The available viscosity grades of HPC [viscosity value (mPa·s) at HPC concentration of 2% and 20° C.] for each particle size are SSL (2.0 to 2.9), SL (3.0 to 5.9), L (6.0 to 10), M (150 to 400), and H (1000 to 4000) in ascending order of viscosity.

When HPC is used as the hydrophilic gel-forming polymer material, this HPC preferably has a particle size corresponding to the fine powder grade (100-mesh sieve passing rate of 99%, average particle size: 150 microns) and a viscosity corresponding to the grade M (150 to 400 mPa·s) or H (1000 to 4000 mPa·s).

Also, HPC may be used as a binder for coating of the matrix preparation of the present invention. When HPC is used as the binder, this HPC is usually dissolved in water or an organic solvent such as an alcohol and used as a solution. In this case, a particle size corresponding to the regular powder grade is acceptable for the hydroxypropyl cellulose, and its viscosity is preferably one corresponding to the grades L (6.0 to 10.0), SL (3.0 to 5.9), and SSL (2.0 to 2.9), more preferably the grade SL (3.0 to 5.9).

The "excipient (D)" according to the present invention means a water-soluble or water-insoluble excipient.

Of these, examples of the water-soluble excipient can include the following (1) and (2):
(1) saccharides such as fructose, purified sucrose, sucrose, purified sucrose spherical granules, lactose, anhydrous lactose, sucrose-starch spherical granules, semi-digested starch, glucose, glucose hydrate, powder sugar, pullulan, β-cyclodextrin, mannitol, xylitol, and erythritol; and
(2) nonionic water-soluble polymers such as povidone (PVP; polyvinylpyrrolidone), polyethylene glycol (PEG), polypropylene glycol, polyvinyl alcohol, and polyoxyethylene oxide.

Examples of the water-insoluble excipient can include L-aspartic acid, alginic acid, carmellose sodium, hydrous silicon dioxide, crospovidone, calcium glycerophosphate, magnesium silicate aluminate, calcium silicate, magnesium silicate, light anhydrous silicic acid, crystalline cellulose, cellulose powder, synthetic aluminum silicate, synthetic aluminum silicate/hydroxypropyl starch/crystalline cellulose, flour, wheat starch, wheat germ flour, wheat germ oil, rice powder, rice starch, cellulose acetate phthalate, titanium oxide, magnesium oxide, dihydroxyaluminum aminoacetate, calcium tertiary phosphate, talc, calcium carbonate, magnesium carbonate, precipitated calcium carbonate, natural aluminum silicate, corn starch, granulated corn starch, potato starch, hydroxypropyl cellulose, hydroxypropyl starch, calcium hydrogenphosphate anhydrous, granulated calcium hydrogenphosphate anhydrous, and calcium dihydrogenphosphate.

The "excipient (D)" according to the present invention is preferably a water-soluble excipient. The water-soluble excipient is preferably a saccharide or a nonionic water-soluble polymer.

The nonionic water-soluble polymer is preferably povidone (PVP: polyvinylpyrrolidone). The povidone according to the present invention means a linear polymer of 1-vinyl-2-pyrrolidone, not crospovidone, which is a cross-linked polymer of 1-vinyl-2-pyrrolidone. Preferable examples of the povidone can include commercially available Kollidon 30 (BASF Japan Ltd.).

The saccharide is preferably lactose or a sugar alcohol. The lactose encompasses all of lactose hydrates and lactose anhydrides. A lactose hydrate is preferred. The sugar alcohol is preferably mannitol, xylitol, and erythritol, particularly preferably mannitol.

The "excipient (D)" according to the present invention is preferably a water-soluble excipient. The water-soluble excipient is preferably a saccharide or a nonionic water-soluble polymer povidone. The saccharide is preferably lactose or a sugar alcohol. The sugar alcohol is preferably mannitol, xylitol, or erythritol, particularly preferably mannitol.

In addition to the pharmacologically active drug (A), the pH-dependent polymer base (B), the hydrophilic gel-forming polymer material (C), and the excipient (D), the sustained-release matrix preparation of the present invention can further contain one or two or more organic acids. The organic acid is effective for improvement in the dissolution properties of the solid preparation in the lower gastrointestinal tract, which is an environment with little water, such as the large intestine.

The organic acid according to the present invention is preferably fumaric acid, succinic acid, alginic acid, adipic acid, citric acid, L-aspartic acid, malonic acid, maleic acid, DL-malic acid, or tartaric acid, more preferably fumaric acid or alginic acid, particularly preferably fumaric acid.

In addition to the pharmacologically active drug (A), the pH-dependent polymer base (B), the hydrophilic gel-forming polymer material (C), and the excipient (D), the sustained-release matrix preparation of the present invention may further contain a disintegrant, a binder, a fluidizing agent, a lubricant, a coloring agent, a polishing agent, etc., so long as the effects of the present invention are not impaired.

Examples of the disintegrant include adipic acid, alginic acid, gelatinized starch, sodium carboxymethyl starch, hydrous silicon dioxide, calcium citrate, light anhydrous silicic acid, synthetic aluminum silicate, wheat starch, rice starch, calcium stearate, corn starch, tragacanth powder, potato starch, hydroxypropyl starch, pregelatinized starch, monosodium fumarate, anhydrous citric acid, and calcium dihydrogenphosphate.

Examples of the binder include maltose syrup powder, gum arabic, gum arabic powder, sodium alginate, propylene glycol alginate ester, hydrolyzed gelatin powder, hydrolyzed starch-light anhydrous silicic acid, fructose, hydrous silicon dioxide, agar powder, light anhydrous silicic acid, synthetic aluminum silicate, wheat flour, wheat starch, rice flour, rice starch, polyvinyl acetate resin, cellulose acetate phthalate, dioctyl sodium sulfosuccinate, dihydroxyaluminum aminoacetate, sodium potassium tartrate, water, sucrose fatty acid ester, purified gelatin, gelatin, D-sorbitol, dextrin, starch, corn starch, tragacanth, tragacanth powder, concentrated glycerin, potato starch, hydroxypropyl starch, vinylpyrrolidone-vinyl acetate copolymers, piperonyl butoxide, glucose, pregelatinized starch, pullulan, polyvinyl alcohol (completely saponified product), polyvinyl alcohol (partially saponified product), and sodium polyphosphate.

Examples of the fluidizing agent can include hydrous silicon dioxide, light anhydrous silicic acid, synthetic aluminum silicate, titanium oxide, stearic acid, calcium stearate, magnesium stearate, calcium tertiary phosphate, talc, corn starch, and magnesium aluminometasilicate.

Examples of the lubricant include cocoa fat, carnauba wax, hydrous silicon dioxide, dry aluminum hydroxide gel, glycerin fatty acid ester, magnesium silicate, light anhydrous silicic acid, hardened oil, synthetic aluminum silicate, white beeswax, magnesium oxide, sodium potassium tartrate, sucrose fatty acid ester, stearic acid, calcium stearate, magnesium stearate, stearyl alcohol, polyoxyl 40 stearate, cetanol, soybean hardened oil, gelatin, talc, magnesium carbonate, precipitated calcium carbonate, corn starch, potato starch, stearyl sodium fumarate, beeswax, magnesium metasilicate aluminate, sodium laurate, and magnesium sulfate.

Examples of the coloring agent can include yellow iron sesquioxide, iron sesquioxide, titanium oxide, orange essence, brown iron oxide, β-carotene, black iron oxide, food blue No. 1, food blue No. 2, food red No. 2, food red No. 3, food red No. 102, food yellow No. 4, and food yellow No. 5.

Examples of the polishing agent include carnauba wax, hardened oil, a polyvinyl acetate resin, white beeswax, titanium oxide, stearic acid, calcium stearate, polyoxyl 40 stearate, magnesium stearate, purified shellac, purified paraffin/carnauba wax mixture, cetanol, talc, colored silver foil, white shellac, paraffin, povidone, Macrogol 1500, Macrogol 4000, Macrogol 6000, beeswax, glycerin monostearate, and rosin.

No particular limitation is imposed on the dosage form of the sustained-release matrix preparation of the present invention, so long as the solid preparation thereof can be orally administered to a subject. However, a tablet or granules are preferred, with a tablet being more preferred.

Hereinafter, another embodiment of the present invention will be described.

The sustained-release preparation of the present invention is a sustained-release preparation obtained by mixing of (A) a pharmacologically active drug, (B) hydroxypropyl methylcellulose acetate succinate (HPMCAS) having an average particle size $D_{50}$ of 20 μm or smaller, (C) hydroxypropyl cellulose (HPC) or hydroxypropyl methylcellulose (HPMC), and (D) a saccharide or a nonionic water-soluble polymer followed by molding.

The preparation of the present invention is characterized in that it is obtained by mixing of the components (A), (B), (C), and (D) followed by molding. The present invention does not encompass, for example, a preparation obtained by mixing of the components (A), (C), and (D) followed by molding, wherein the preparation is provided with coating containing the component (B). However, the present invention encompasses, for example, a preparation obtained by mixing of the components (A), (B), (C), and (D) followed by molding, wherein the preparation is provided with coating containing the component (B).

Examples of the "pharmacologically active drug" used as the component (A) in the preparation of the present invention can include the compounds described above. Also, the "pharmacologically active drug" may be a prodrug that can be converted to the pharmacologically active drug in vivo. The content of the component (A) in the preparation of the present invention is preferably 0.1 to 60% by weight, more preferably 1 to 50% by weight, even more preferably 2 to 35% by weight, particularly preferably 3 to 25% by weight.

Examples of the "hydroxypropyl methylcellulose acetate succinate (HPMCAS)" used as the component (B) in the preparation of the present invention can include the substances described above. The grade of HPMCAS is preferably HF, MF, or LF, more preferably LF.

Moreover, HPMCAS used as the component (B) in the preparation of the present invention has an average particle size ($D_{50}$) of 20 μm or smaller, preferably 10 μm or smaller, more preferably 5 μm or smaller. Moreover, its 90% cumulative particle size $D_{90}$ in which the cumulative fraction of the particles is 90% is preferably 20 μm or smaller, more preferably 11 μm or smaller. HPMCAS preferably has particle sizes $D_{50}$ of 10 μm or smaller and $D_{90}$ of 20 μm or smaller, more preferably $D_{50}$ of 5 μm or smaller and $D_{90}$ of 11 μm or smaller.

In the present specification, the term "$D_{50}$" refers to a particle size corresponding to the median value of a cumulative distribution curve determined using a laser diffraction-type meter HELOS (Japan Laser Corp.), i.e., a median size. Also, in the present specification, the term "$D_{90}$" refers to a particle size corresponding to 90% of the cumulative distribution curve determined using the HELOS. For example, $D_{90}$ of 20 μm means that 90% of the measured powders have a particle size of 20 μm or smaller and the remaining 10% have a particle size larger than 20 μm.

The content of the component (B) in the preparation of the present invention is preferably 10 to 95% by weight, more preferably 15 to 80% by weight, even more preferably 20 to 50% by weight, particularly preferably 25 to 45% by weight.

Examples of the "cellulose derivative" used as the component (C) in the preparation of the present invention can include the substances described above. Hydroxypropyl cellulose (HPC) and hydroxypropyl methylcellulose (HPMC) are preferred, with HPC being more preferred.

When HPC is used as the component (C), a fine powder grade (100-mesh sieve passing rate of 99%) and grade M (viscosity: 150 to 400 mPa·s) or H (viscosity: 1000 to 4000 mPa·s) are preferred.

The content of the component (C) in the preparation of the present invention is preferably 3 to 50% by weight, more preferably 4 to 40% by weight, even more preferably 5 to 35% by weight.

Moreover, in the preparation of the present invention, HPC is used as the component (C) and may also be used as a binder. In this case, HPC may be a fine powder grade or a regular powder grade and is not limited by viscosity, so long as it can be used as a binder. Grade L (6.0 to 10.0 mPa·s), SL (3.0 to 5.9 mPa·s), SSL (2.0 to 2.9 mPa·s), or the like is preferred, with grade SL being more preferred.

Examples of the saccharide or the nonionic water-soluble polymer used as the component (D) in the preparation of the present invention can include the substances described above.

The saccharide is preferably lactose or a sugar alcohol. The lactose may be a lactose hydrate or a lactose anhydride and is preferably a lactose hydrate. The sugar alcohol is preferably mannitol, xylitol, or erythritol, more preferably mannitol.

Examples of the nonionic water-soluble polymer can include the substances described above. Povidone (PVP: polyvinylpyrrolidone) is preferred. The povidone used as the component (D) is a linear polymer of 1-vinyl-2-pyrrolidone, not crospovidone, which is a cross-linked polymer of 1-vinyl-2-pyrrolidone.

The content of the component (D) in the preparation of the present invention is preferably 5 to 50% by weight. When the component (D) is lactose, the content of the lactose in the preparation is preferably 10 to 20%. When the component (D) is a sugar alcohol, the content of the sugar alcohol in the preparation is preferably 5 to 35%, more preferably 10 to 33%. When the component (D) is povidone, the content of the povidone in the preparation is preferably 20 to 45%.

In addition to the components (A) to (D), the preparation of the present invention may further contain an organic acid.

The organic acid is preferably fumaric acid, succinic acid, alginic acid, adipic acid, citric acid, L-aspartic acid, malonic acid, maleic acid, DL-malic acid, or tartaric acid, more preferably fumaric acid or alginic acid, particularly preferably fumaric acid.

When the preparation of the present invention contains an organic acid, the content of the organic acid in the preparation is preferably 10 to 40% by weight.

The preparation of the present invention may further contain the disintegrant, the binder, the fluidizing agent, the lubricant, the coloring agent, the polishing agent, etc., so long as the effects of the present invention are not impaired.

The preparation of the present invention is produced by mixing of the components (A) to (D) followed by molding. Alternatively, the preparation of the present invention is produced by granulation of a mixture of the components (A) to (D) followed by molding. The mixing, granulation, and molding can be performed using methods well known in the art. When the molding is compression molding, the pressure of compression is preferably 6 to 15 kN. The preparation of the present invention may be coated. The coated preparation of the present invention can be produced by spraying of a coating solution onto molded tablets. The coating can be performed using methods well known in the art. When the preparation of the present invention contains additional additives, these additives may be added thereto in any of mixing, granulation, compression, and coating steps.

No particular limitation is imposed on the shape of the preparation of the present invention. However, a lens, disc, round, oval, almond, teardrop, or polygonal (triangle or rhombus) shape is preferred.

The composition containing the components (A) to (D) of the present invention has a favorable tablet strength that prevents dose dumping in an acidic solution, and has favorable dissolution properties in a neutral solution. Thus, the composition of the present invention is effective for maintenance of prolonged dissolution of the "pharmacologically active drug" contained therein as the component (A) from the duodenum through the small intestine to the lower gastrointestinal tract.

EXAMPLES

Next, the present invention will be described in detail with reference to Examples. However, the present invention is not intended to be limited to these by any means.

Abbreviations used in Examples are as follows:

HPC-M fine: hydroxypropyl cellulose grade M fine powder grade (99% particles of which pass through a 100-mesh sieve) (manufactured by Nippon Soda Co., Ltd.)

HPC-SL regular: hydroxypropyl cellulose grade SL regular powder grade (99% particles of which pass through a 40-mesh sieve) (manufactured by Nippon Soda Co., Ltd.)

HPC-H fine: hydroxypropyl cellulose grade H fine powder grade (99% particles of which pass through a 100-mesh sieve) (manufactured by Nippon Soda Co., Ltd.)

HPMCAS-LF: hydroxypropyl methylcellulose acetate succinate grade LF ($D_{50}$: 5 μm, $D_{90}$: 11 μm) (manufactured by Shin-Etsu Chemical Co., Ltd.)

HPMCAS-LG: hydroxypropyl methylcellulose acetate succinate grade LG ($D_{50}$: 49 μm, $D_{90}$: 100 μm) (manufactured by Shin-Etsu Chemical Co., Ltd.)

$D_{50}$ and $D_{90}$ were measured at a dispersion pressure of 3 bar in a measurement range of R4 using a laser diffraction-type particle size distribution meter HELOS&RODOS (Japan Laser Corp.).

Tests on dissolution properties in an acidic or neutral solution were conducted as follows:

(Dissolution Test in Acidic Solution)

The dissolution test was conducted by the paddle method at rotation rates of 50 rpm and 200 rpm at 37±0.5° C. in 0.01 N hydrochloric acid (900 mL), and the time-dependent average percentage dissolution of a drug in the dissolution medium was calculated. The average percentage dissolution at each rotation rate, the difference in the average percentage dissolution of the drug (value at the rotation rate of 200 rpm in the paddle method–value at the rotation rate of 50 rpm in the paddle method: $D_{2h,200rpm} - D_{2h,50rpm}$), and the average percentage dissolution ratio (value at the rotation rate of 200 rpm in the paddle method/value at the rotation rate of 50 rpm in the paddle method: $D_{2h,200rpm}/D_{2h,50rpm}$) derived from the dissolution test for 2 hours were calculated.

(Dissolution Test in Neutral Solution)

The dissolution test was conducted by the paddle method at a rotation rate of 50 rpm at 37±0.5° C. in phosphate buffer (pH 6.8, 900 mL), and the time-dependent average percentage dissolution of a drug in the dissolution medium was calculated.

Example 1

Figure 1:
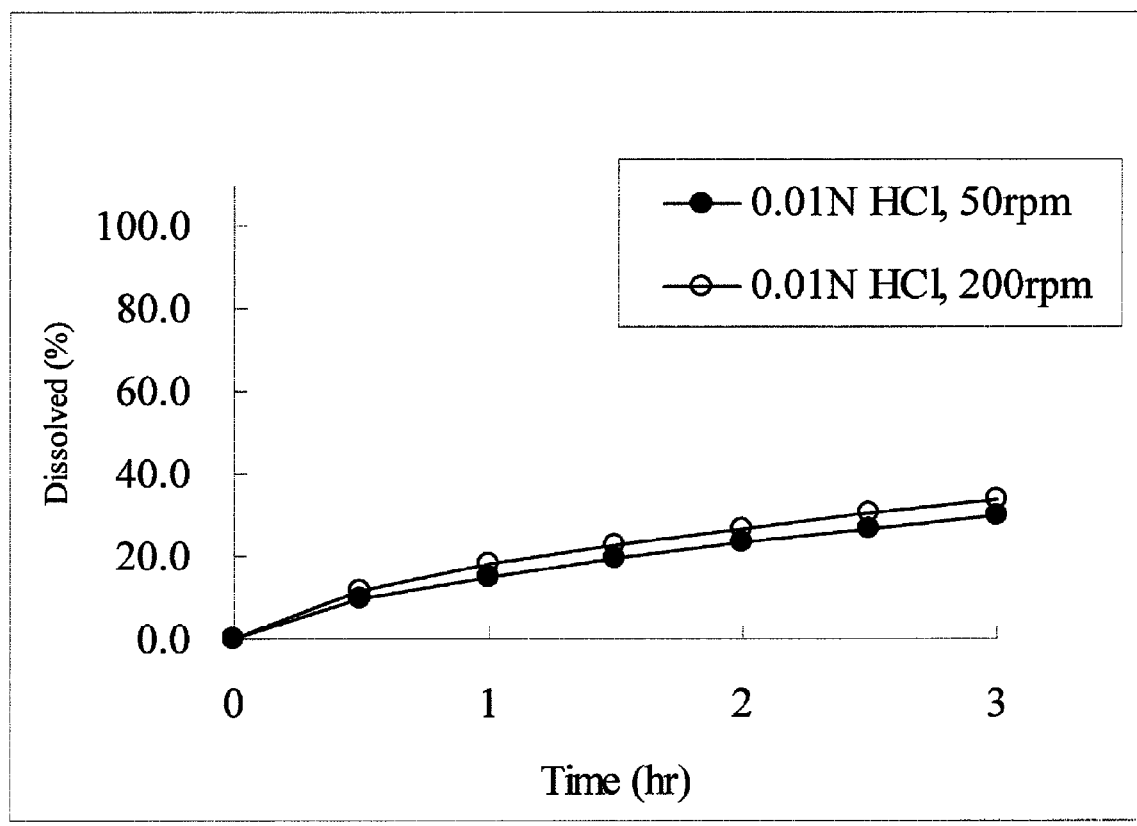
FIG. 1 is a diagram showing dissolution properties in an acidic solution (the paddle method, dissolution test medium: 0.01 N hydrochloric acid (900 mL), paddle rotation rate: 50 rpm and 200 rpm) for tablets having formulation 1.
Figure 2:
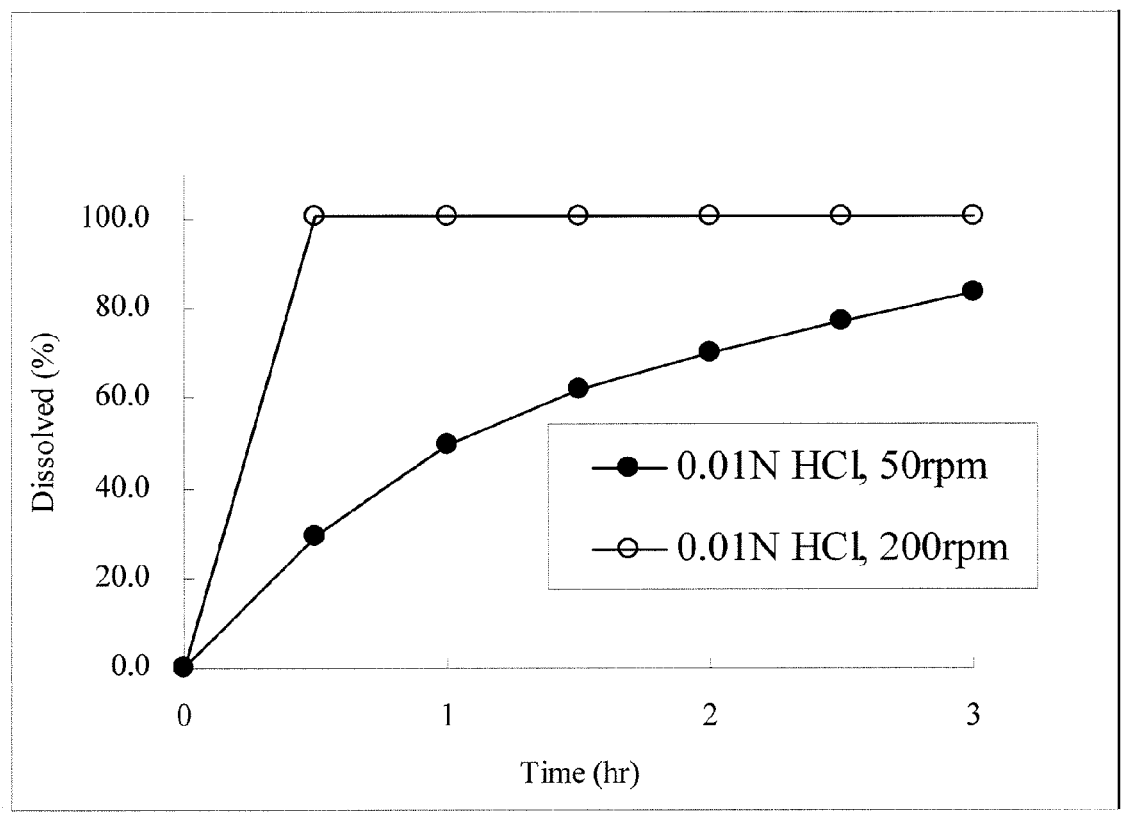
Figure 3:
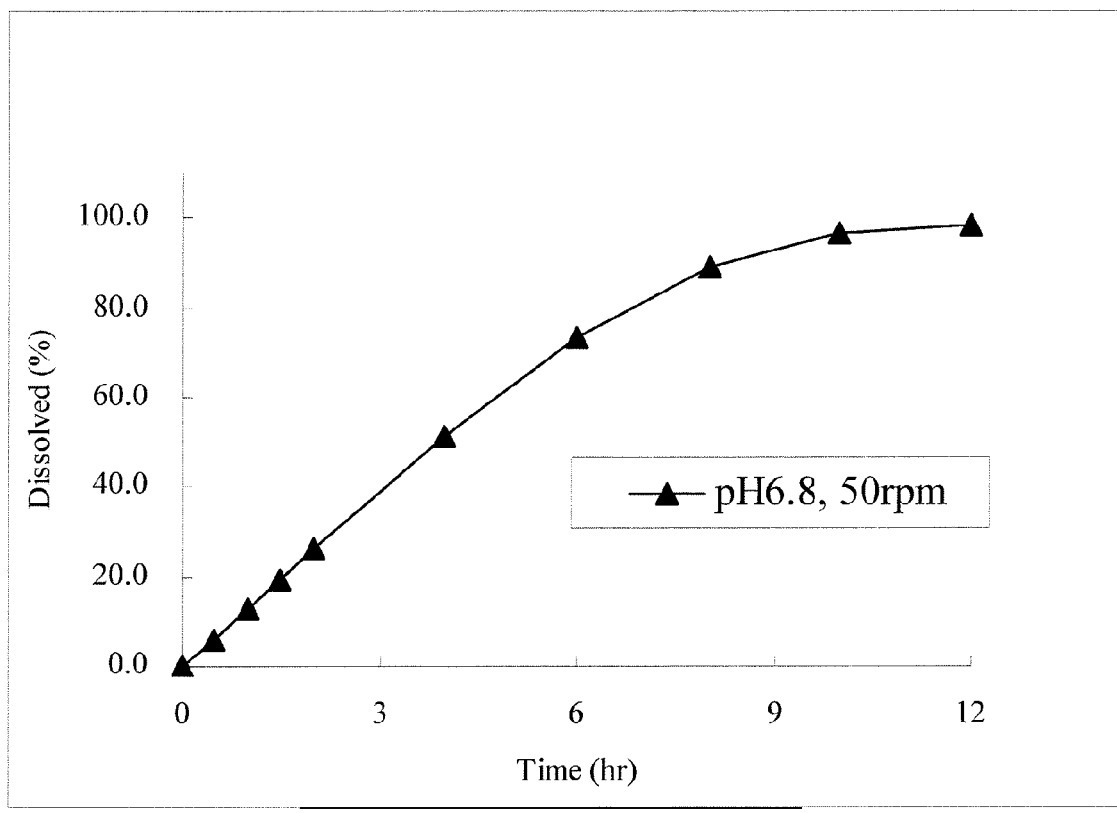
FIG. 3 is a diagram showing dissolution properties in a neutral solution (the paddle method, 900 mL, 50 rpm; dissolution test medium: phosphate buffer, pH 6.8) for tablets having formulation 1.
Figure 4:
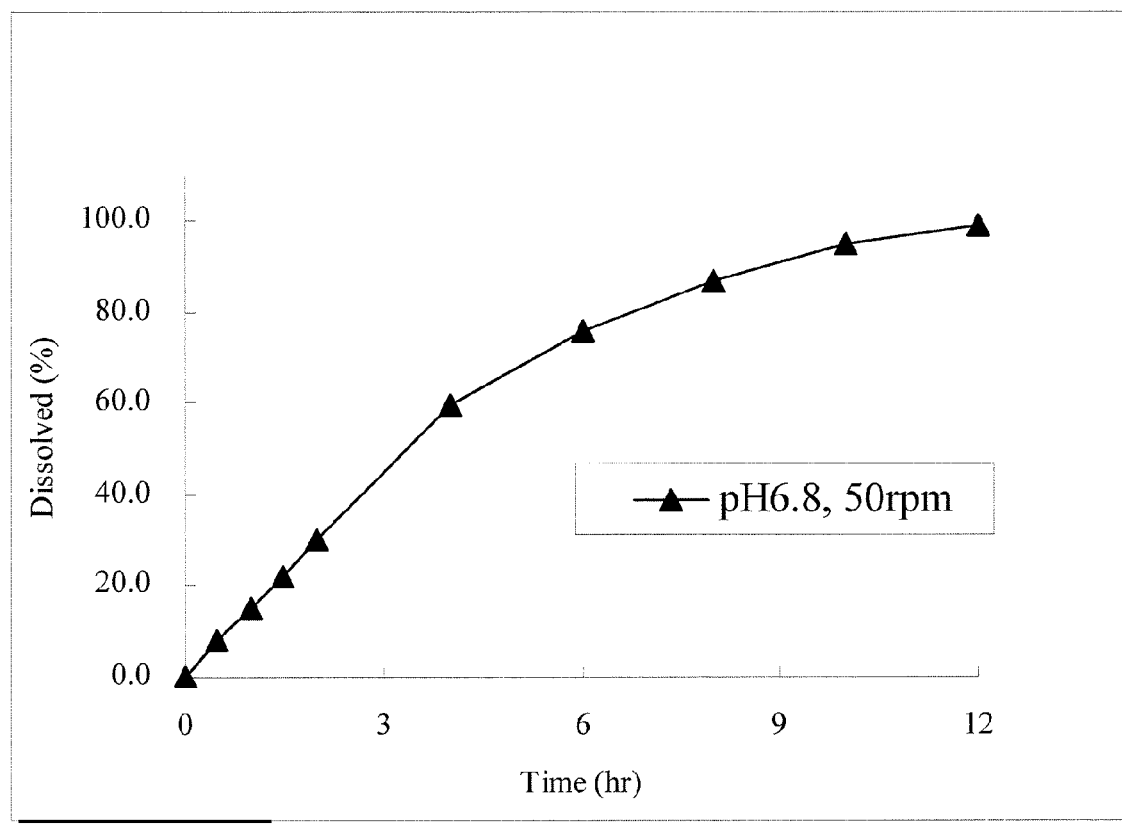

Tablets having formulations 1 and 1a shown in Table 1 were produced by mixing of each component using a mortar followed by the direct compression method and subjected to the dissolution test in an acidic or neutral solution. The results obtained from the acidic solution are shown in Table 2 and FIGS. 1 and 2. The results obtained from the neutral solution are shown in FIGS. 3 and 4.

TABLE 1

| | Content (mg) | |
|---|---|---|
| | Formulation 1 | Formulation 1a |
| Compound (1a) | 36.4 | 36.4 |
| HPC-M fine | 60.0 | 60.0 |
| HPC-SL regular | 12.0 | 12.0 |
| HPMCAS-LF | 120.0 | — |
| Mannitol | 59.6 | 179.6 |
| Sodium stearyl fumarate | 12.0 | 12.0 |
| Total | 300.0 | 300.0 |

TABLE 2

Influence of paddle rotation rate in acidic test medium on tablets having formulations 1 and 1a

| | Formulation 1 | Formulation 1a |
|---|---|---|
| $D_{2\,h,\,200\,rpm} - D_{2\,h,\,50\,rpm}$ | 3.6% | 30.6% |
| $D_{2\,h,\,200\,rpm} / D_{2\,h,\,50\,rpm}$ | 1.2 | 1.4 |

<Test Results>

As is evident from FIGS. 3 and 4, both the tablets of formulations 1 and 1a exhibited prolonged dissolution properties in the neutral solution. On the other hand, it was demonstrated that the tablets of formulation 1a were largely influenced by the paddle rotation rate in the acidic solution, whereas the tablets of formulation 1 were hardly influenced by the paddle rotation rate even in the acidic solution.

Example 2

Figure 5:
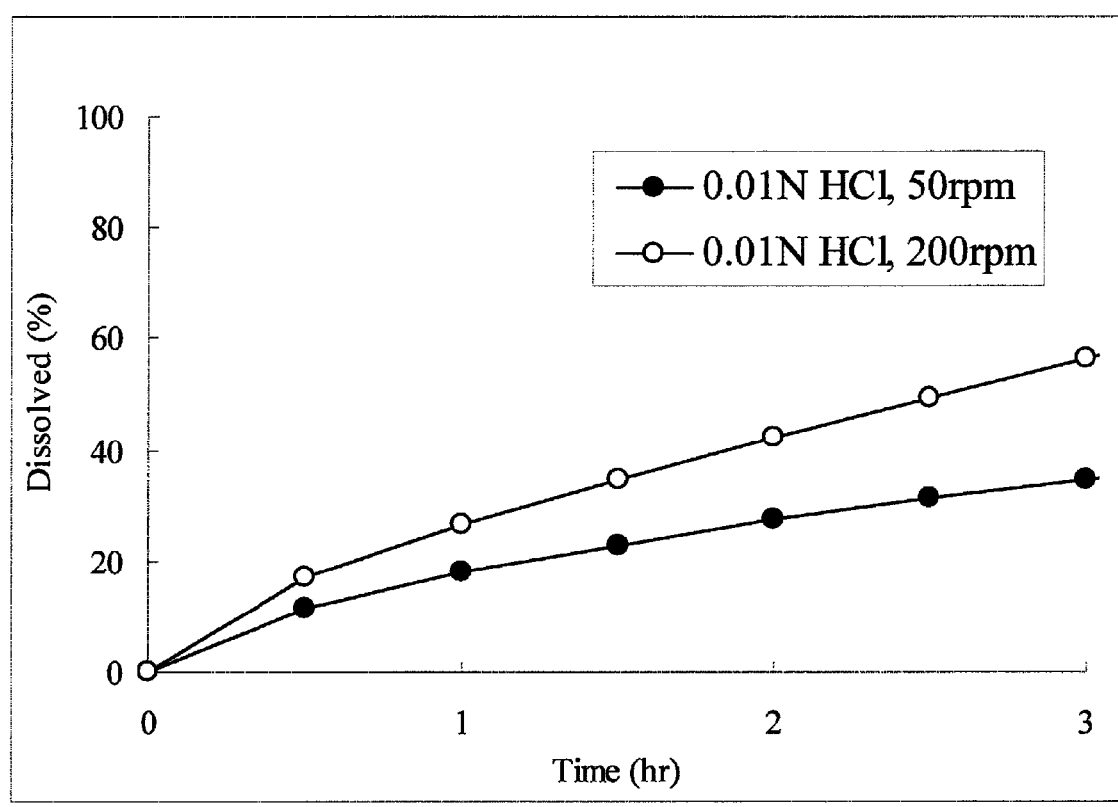

Tablets having formulations 1 and 2a shown in Table 3 were produced by mixing of each component using a mortar followed by the direct compression method and subjected to the dissolution test in an acidic solution. The results are shown in Table 4 and FIGS. 1 and 5.

TABLE 3

| | Content (mg) | |
|---|---|---|
| | Formulation 1 | Formulation 2a |
| Compound (1a) | 36.4 | 36.4 |
| HPC-M fine | 60.0 | 60.0 |
| HPC-SL regular | 12.0 | 12.0 |
| HPMCAS-LF | 120.0 | — |
| HPMCAS-LG | — | 120.0 |
| Mannitol | 59.6 | 59.6 |
| Sodium stearyl fumarate | 12.0 | 12.0 |
| Total | 300.0 | 300.0 |

TABLE 4

Influence of paddle rotation rate in acidic test medium on tablets having formulations 1 and 2a

| | Formulation 1 | Formulation 2a |
|---|---|---|
| $D_{2\ h,\ 200\ rpm} - D_{2\ h,\ 50\ rpm}$ (%) | 4.3 | 15.0 |
| $D_{2\ h,\ 200\ rpm} / D_{2\ h,\ 50\ rpm}$ | 1.2 | 1.6 |

<Test Results>

The tablets of formulation 1 in which HPMCAS having a small particle size was used were less influenced by the paddle rotation rate in the acidic solution, than the tablets of formulation 2a in which HPMCAS having a large particle size was used. Thus, HPMCAS having a small particle size was effective for maintenance of tablet strength.

Example 3

Figure 6:
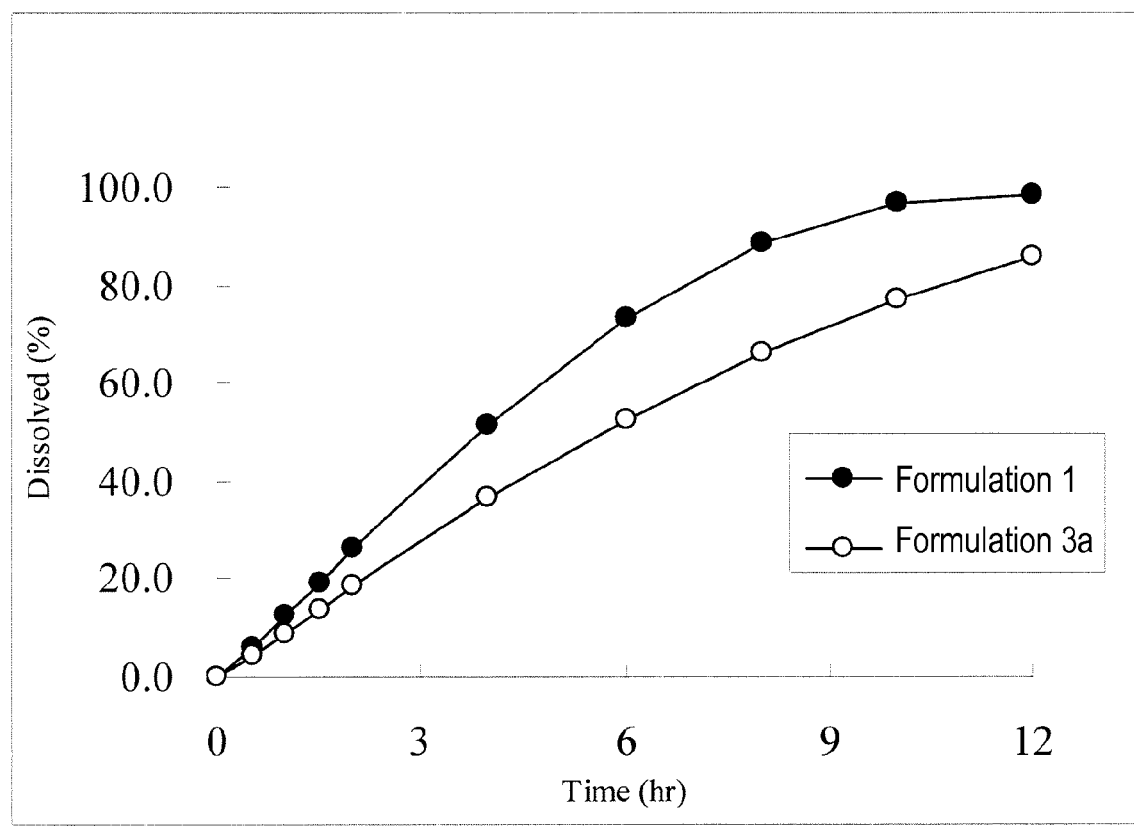

Tablets having formulations 1 and 3a shown in Table 5 were produced by mixing of each component using a mortar followed by the direct compression method and subjected to the dissolution test in a neutral solution, a dissolution test using USP Apparatus 3, and in vivo absorption property evaluation using dogs. The results of the dissolution test in the neutral solution are shown in FIG. 6.

TABLE 5

| | Content (mg) | |
|---|---|---|
| | Formulation 1 | Formulation 3a |
| Compound (1a) | 36.4 | 36.4 |
| HPC-M fine | 60.0 | 60.0 |
| HPC-SL regular | 12.0 | 12.0 |
| HPMCAS-LF | 120.0 | 120.0 |
| Mannitol | 59.6 | — |
| Microcrystalline cellulose [a] | — | 59.6 |
| Sodium stearyl fumarate | 12.0 | 12.0 |
| Total | 300.0 | 300.0 |

[a] grade PH101

<Test Results>

As shown in FIG. 6, the tablets obtained using mannitol or crystalline cellulose exhibited prolonged drug dissolution in the neutral solution. On the other hand, the dissolution test using USP Apparatus 3 showed that the tablets of formulation 1 in which mannitol was used exhibited prolonged drug dissolution, whereas the tablets of formulation 3a in which crystalline cellulose was used tended to have a sluggish dissolution rate of less than 100%. Moreover, the tablets of formulation 1 in which mannitol was used were effective for improvement in bioavailability (BA) in the in vivo absorption property evaluation using dogs.

Example 4

Figure 7:
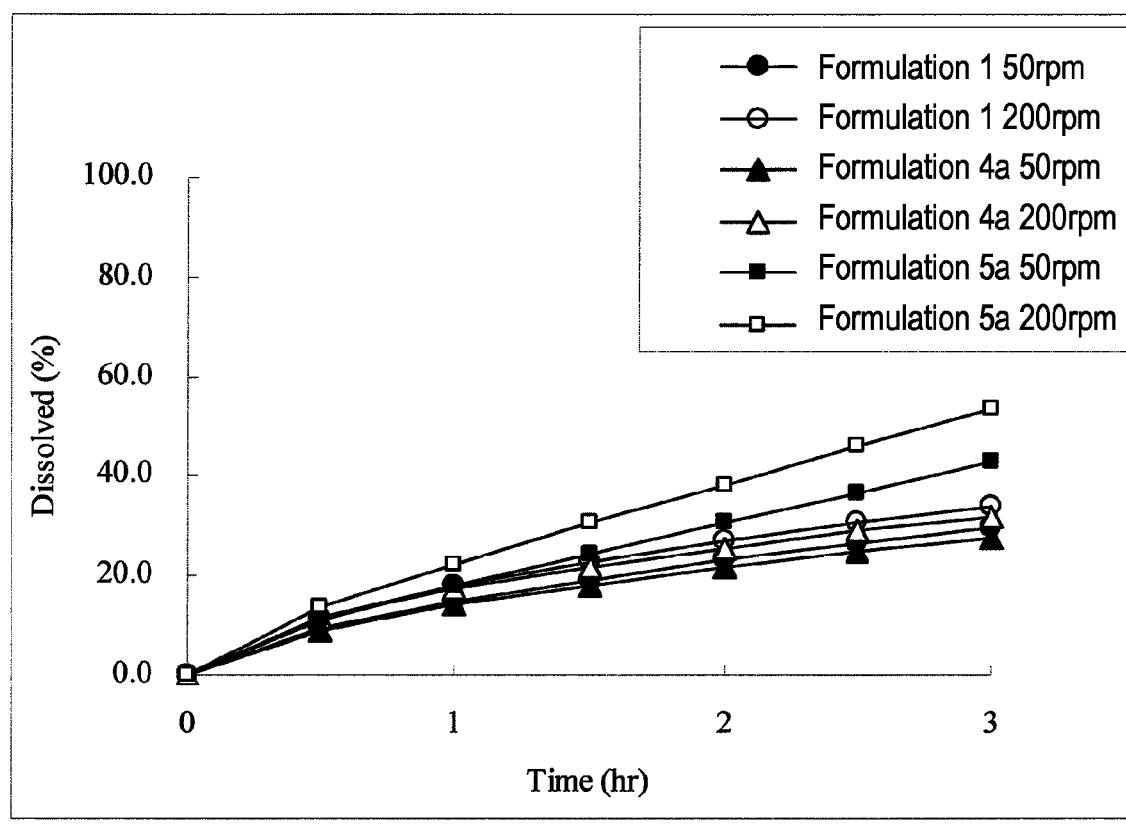
Figure 8:
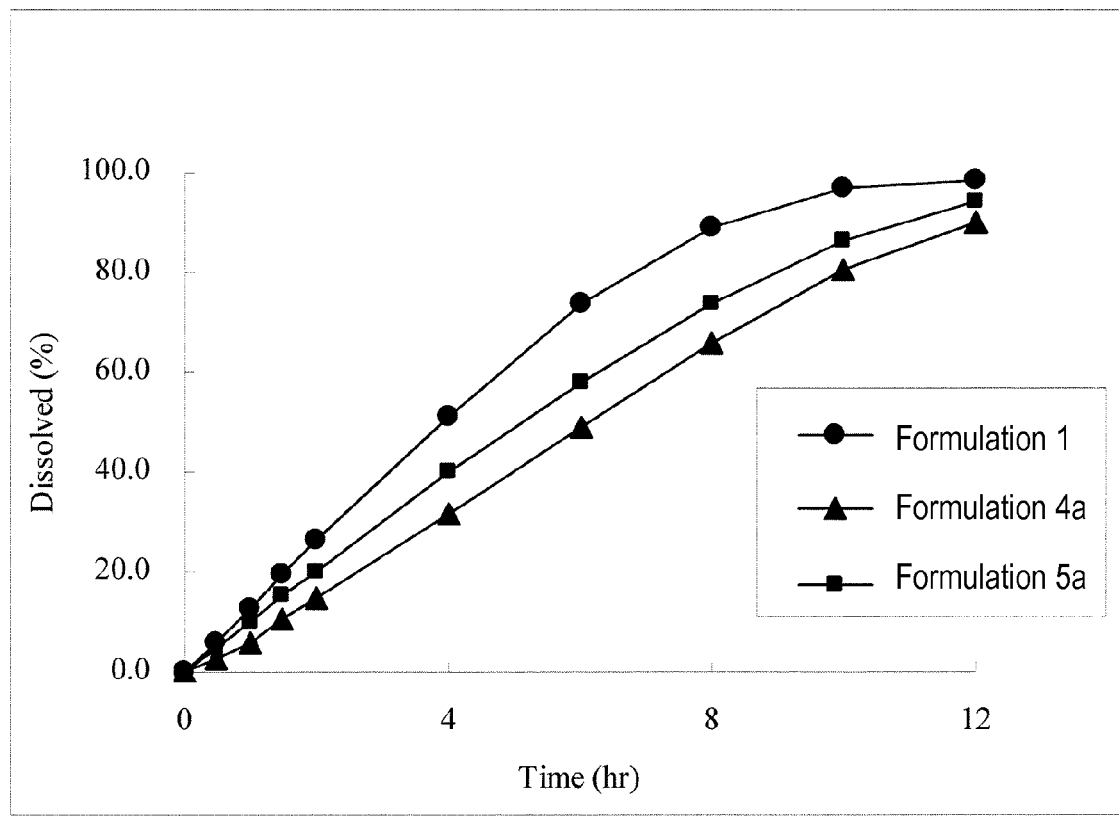

Tablets having formulations 1, 4a, and 5a shown in Table 6 were produced by mixing of each component using a mortar followed by the direct compression method and subjected to the dissolution test in an acidic or neutral solution. The results obtained from the acidic solution are shown in Table 7 and FIG. 7. The results obtained from the neutral solution are shown in FIG. 8.

TABLE 6

| | Content (mg) | | |
|---|---|---|---|
| | Formulation 1 | Formulation 4a | Formulation 5a |
| Compound (1a) | 36.4 | 36.4 | 36.4 |
| HPC-M fine | 60.0 | 60.0 | 60.0 |
| hpc-sl regular | 12.0 | 12.0 | 12.0 |
| HPMCAS-LF | 120.0 | — | — |
| Methacrylic acid copolymer [a] | — | 120.0 | — |
| Carboxymethylethylcellulose | — | — | 120.0 |
| Mannitol | 59.6 | 59.6 | 59.6 |
| Sodium stearyl fumarate | 12.0 | 12.0 | 12.0 |
| Total | 300.0 | 300.0 | 300.0 |

[a] grade L100-55

TABLE 7

Influence of paddle rotation rate in acidic test medium on tablets having formulations 1, 4a, and 5a

| | Formulation 1 | Formulation 4a | Formulation 5a |
|---|---|---|---|
| $D_{2\ h,\ 200\ rpm} - D_{2\ h,\ 50\ rpm}$ (%) | 3.6 | 3.9 | 7.7 |
| $D_{2\ h,\ 200\ rpm} / D_{2\ h,\ 50\ rpm}$ | 1.2 | 1.2 | 1.3 |

<Test Results>

It was confirmed that all the tablets of these formulations were hardly influenced by the paddle rotation rate in the acidic solution. Moreover, all the tablets of these formulations exhibited prolonged dissolution properties in the neutral solution.

Example 5

Figure 9:
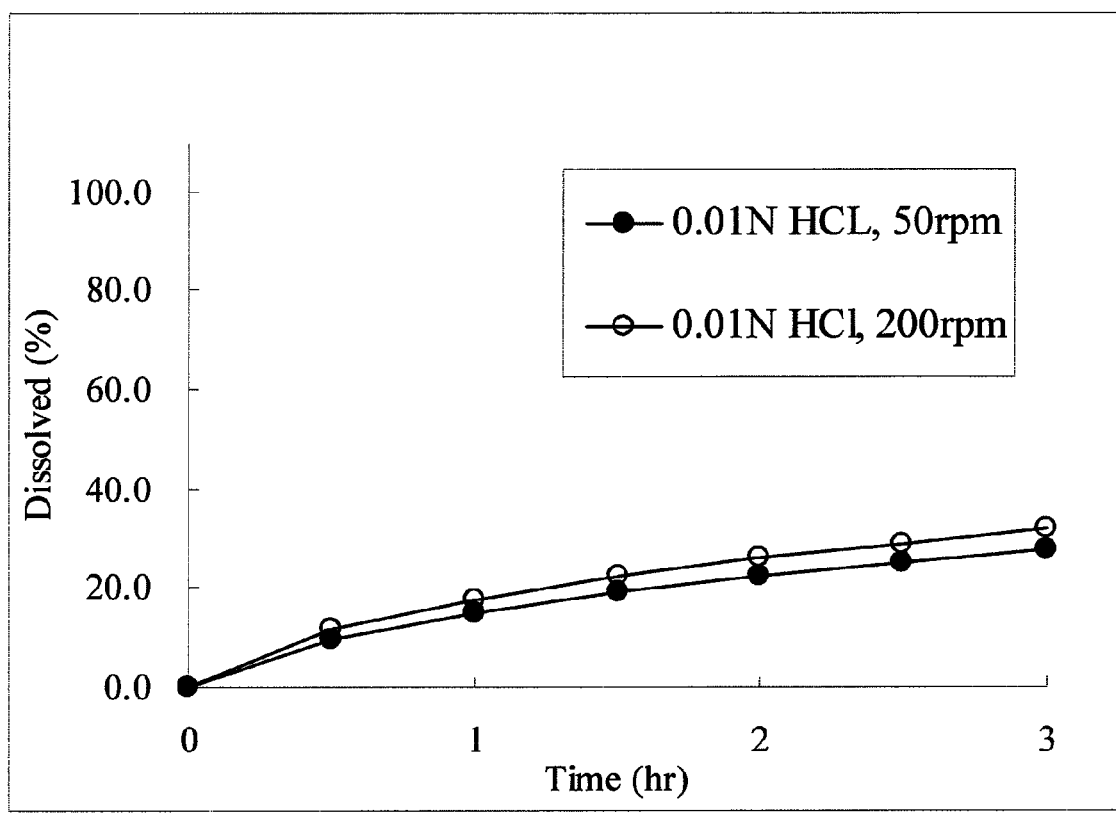
FIG. 9 is a diagram showing dissolution properties in an acidic solution (the paddle method, dissolution test medium: 0.01 N hydrochloric acid (900 mL), paddle rotation rate: 50 rpm and 200 rpm) for tablets having formulation 2.
Figure 10:
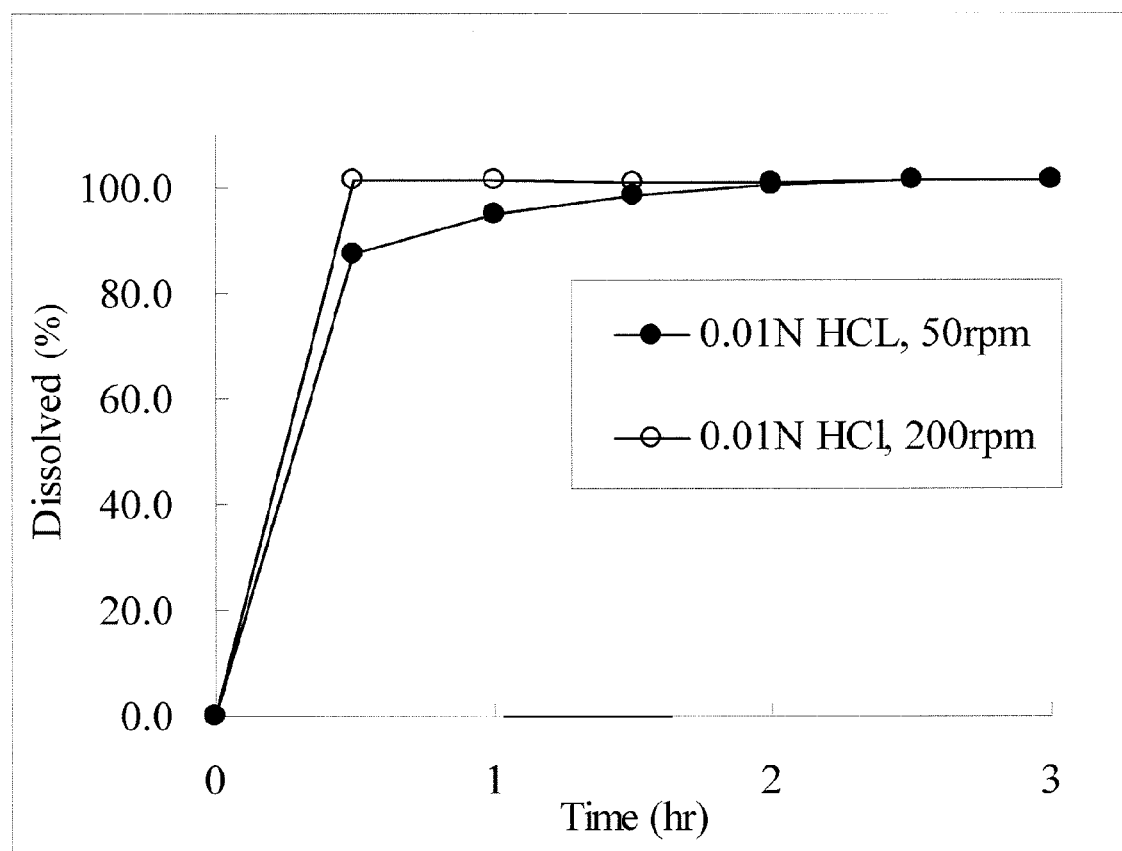
Figure 11:
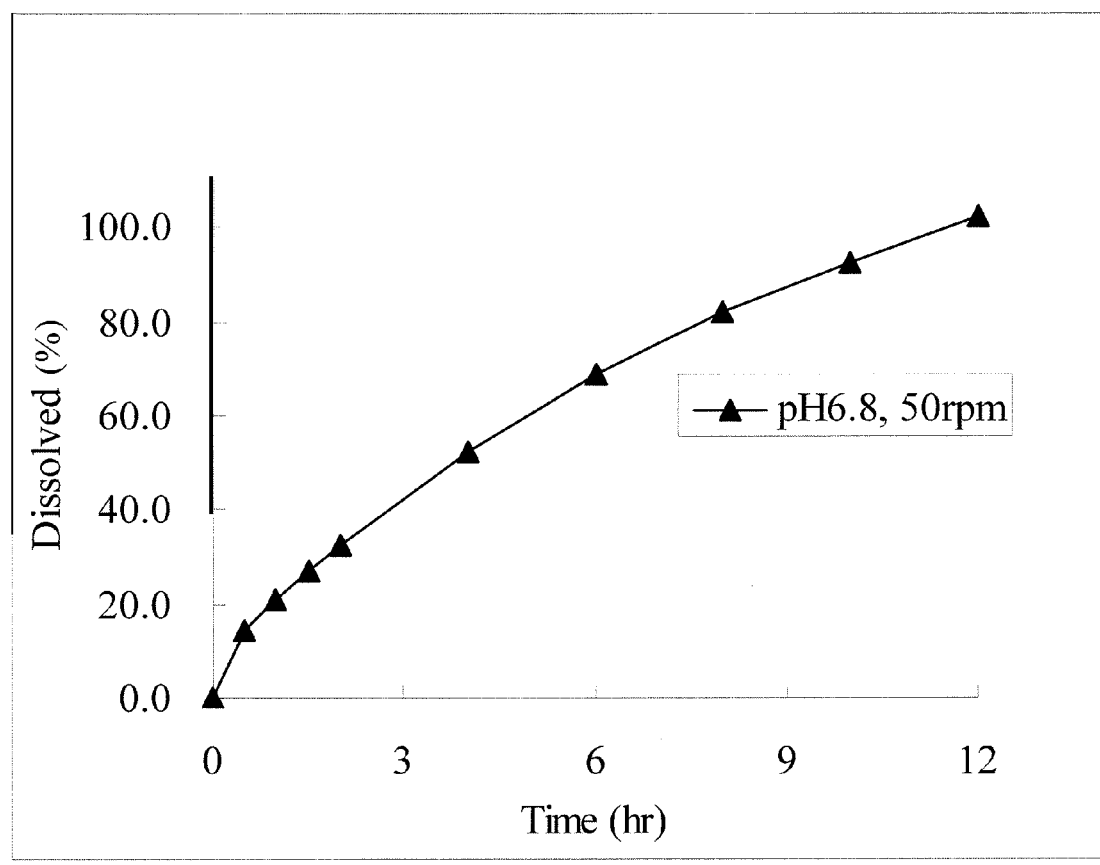
FIG. 11 is a diagram showing dissolution properties in a neutral solution (the paddle method, 900 mL, 50 rpm; dissolution test medium: phosphate buffer, pH 6.8) for tablets having formulation 2.
Figure 12:
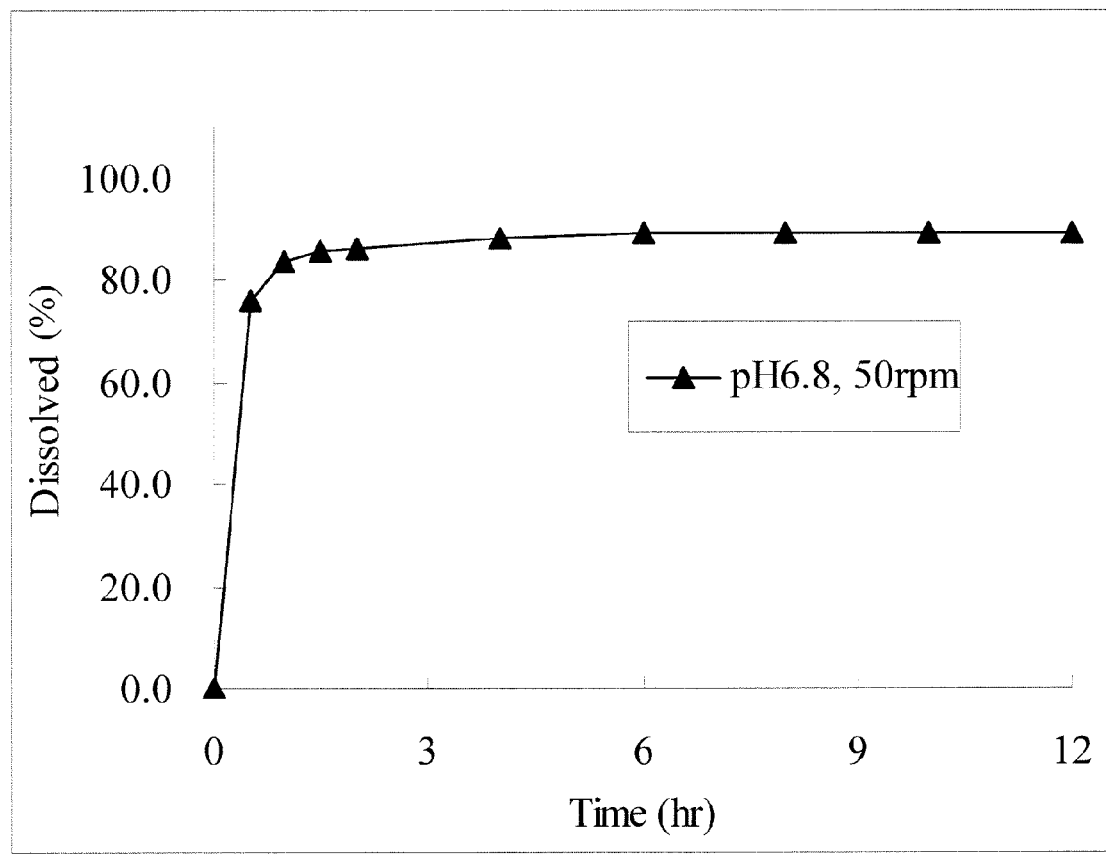

Tablets having formulations 2 and 6a shown in Table 8 were produced by mixing of each component using a mortar followed by the direct compression method and subjected to the dissolution test in an acidic or neutral solution. The results obtained from the acidic solution are shown in FIGS. 9 and 10. The results obtained from the neutral solution are shown in FIGS. 11 and 12.

TABLE 8

| | Content (mg) | |
|---|---|---|
| | Formulation 2 | Formulation 6a |
| Compound (1b) | 80.8 | 80.8 |
| HPC-M fine | 20.0 | 20.0 |

TABLE 8-continued

| | Content (mg) | |
|---|---|---|
| | Formulation 2 | Formulation 6a |
| Fumaric acid [a] | 120.0 | 120.0 |
| HPMCAS-LF | 120.0 | — |
| Lactose [b] | 51.2 | 171.2 |
| Sodium stearyl fumarate | 8.0 | 8.0 |
| Total | 400.0 | 400.0 |

[a] grade 100M;
[b] grade 200M

<Test Results>

The tablets of formulation 2 in which HPMCAS-LF was used were hardly influenced by the paddle rotation rate in the acidic solution and exhibited prolonged dissolution properties in the neutral solution. On the other hand, as shown in FIGS. 10 and 12, the tablets of formulation 6a in which HPMCAS-LF was not used were rapidly dissolved in the acidic and neutral solutions, showing no sustained-release effect.

Example 6

Tablets having formulations 2, 7a, and 7b shown in Table 9 were produced by mixing of each component using a mortar followed by the direct compression method and subjected to the dissolution test in an acidic solution. The results are shown in Table 10 and FIGS. 9, 13, and 14.

TABLE 9

| | Content (mg) | | |
|---|---|---|---|
| | Formulation 2 | Formulation 7a | Formulation 8a |
| Compound (1b) | 80.8 | 80.8 | 80.8 |
| HPC-M fine | 20.0 | 20.0 | 20.0 |
| Fumaric acid [a] | 120.0 | 120.0 | 120.0 |
| HPMCAS-LF | 120.0 | — | — |
| Methacrylic acid copolymer [b] | — | 120.0 | — |
| Carboxymethyl ethyl cellulose | — | — | 120.0 |
| Lactose [c] | 51.2 | 51.2 | 51.2 |
| Sodium stearyl fumarate | 8.0 | 8.0 | 8.0 |
| Total | 400.0 | 400.0 | 400.0 |

[a] grade 100M;
[b] grade L100-55;
[c] grade 200M

TABLE 10

Influence of paddle rotation rate in acidic test medium on tablets having formulations 2, 7a, and 8a

| | Formulation 2 | Formulation 7a | Formulation 8a |
|---|---|---|---|
| $D_{2\,h,\,200\,rpm} - D_{2\,h,\,50\,rpm}$ (%) | 3.6 | 18.1 | −2.0 |
| $D_{2\,h,\,200\,rpm} / D_{2\,h,\,50\,rpm}$ | 1.2 | 1.6 | 1.0 |

<Test Results>

Figure 13:
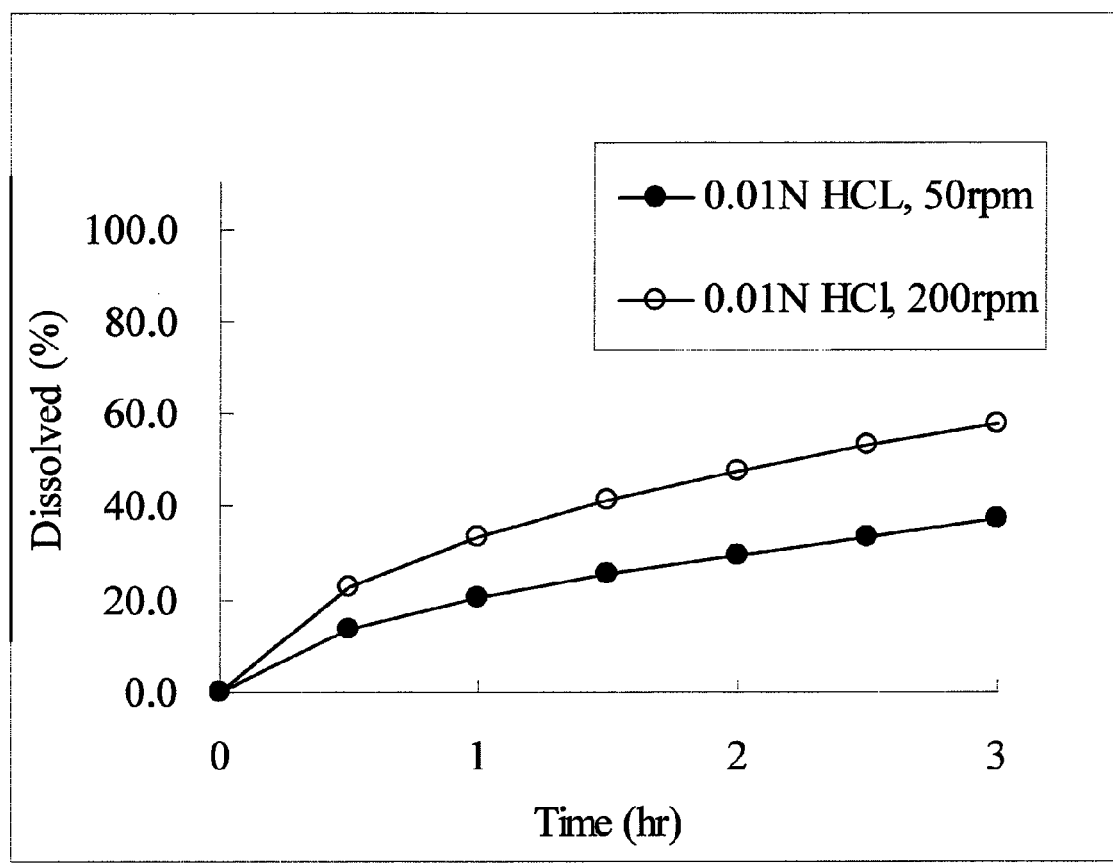
FIG. 13 is a diagram showing dissolution properties in an acidic solution (the paddle method, dissolution test medium.

As shown in FIG. 13, the dissolution rate of the tablets of formulation 7a was more influenced by the paddle rotation rate than that of the tablets of formulation 2. Moreover, as shown in FIG. 14, the tablets of formulation 8a were more rapidly dissolved than the tablets of formulations 2 and 7a and 80% or more dissolved within 30 minutes, showing no sustained-release effect.

Example 7

Ingredients of formulations 9a, 9b, and 9c shown in Table 11, except for HPC-SL regular and sodium stearyl fumarate, were added to a fluidized-bed granulator and mixed. HPC-SL regular was dissolved in water, and the obtained binding solution was sprayed thereon for wet granulation. The obtained granules were dried, and sodium stearyl fumarate was then added to the granules thus granulated, and mixed using a V-shaped mixer to yield granules which were compressed into tablets. The granules were compressed (die: 10 mmϕ) using a rotary tableting machine to yield plain tablets. An aqueous dispersion of a coating base composed of hypromellose 2910, talc, titanium oxide, and polyethylene glycol was sprayed onto the plain tablets using a pan coater to yield film-coated tablets. The obtained tablets were subjected to the dissolution test in an acidic and neutral solution. The results obtained from the acidic solution are shown in Table 12 and FIGS. 15, 16, and 17. The results obtained from the neutral solution are shown in FIGS. 18, 19, and 20.

TABLE 11

| | Content (mg) | | |
|---|---|---|---|
| | Formulation 9a | Formulation 9b | Formulation 9c |
| Compound (1a) | 36.4 | 36.4 | 36.4 |
| HPC-M fine | 15.0 | — | — |
| HPC-H fine | — | 60.0 | 60.0 |
| HPC-SL regular | 12.0 | 12.0 | 8.0 |
| HPMCAS-LF | 120.0 | 120.0 | 90.0 |
| Mannitol | 104.6 | 59.6 | — |
| Povidone | — | — | 93.6 |
| Sodium stearyl fumarate | 12.0 | 12.0 | 12.0 |
| Total | 300.0 | 300.0 | 300.0 |

TABLE 12

Influence of paddle rotation rate in acidic test medium on tablets having formulations 9a to 9c

| | Formulation 9a | Formulation 9b | Formulation 9c |
|---|---|---|---|
| $D_{2\,h,\,200\,rpm} - D_{2\,h,\,50\,rpm}$ (%) | 22.1 | 10.4 | 7.6 |
| $D_{2\,h,\,200\,rpm} / D_{2\,h,\,50\,rpm}$ | 1.5 | 1.5 | 1.3 |

<Test Results>

As shown in Table 12 and FIG. 15 as to dissolution behaviors in the acidic solution, the tablets of formulation 9a had a larger difference in dissolution rate in the acidic solution than that of the tablets of formulations 9b and 9c. As shown in FIG. 18 as to dissolution behaviors in the neutral solution, the tablets of formulation 9a exhibited almost 100% dissolution in approximately 8 hours, which was more rapid than that of the tablets of formulations 9b (FIG. 19) and 9c (FIG. 20).

On the other hand, all the preparations of formulations 9a to 9c exhibited lower Cmax and higher trough concentration (concentration after 24 hours) than those of an administered aqueous solution having the same amount of the drug in a clinical trial using healthy humans, demonstrating that these preparations had properties desired for sustained-release preparations.

Example 8

Tablets having formulation 10 shown in Table 13 were produced by mixing of each component using a mortar followed by the direct compression method and subjected to the dissolution test in acidic and neutral solutions. The results obtained from the acidic solution are shown in Table 14 and FIG. 21. The results obtained from the neutral solution are shown in FIG. 22.

TABLE 13

|  | Content (mg) Formulation 10 |
|---|---|
| Compound (2) | 5.0 |
| HPC-M fine | 50.0 |
| HPMCAS-LF | 50.0 |
| Mannitol | 50.0 |
| Total | 155.0 |

TABLE 14

Influence of paddle rotation rate in acidic test medium on tablets having formulation 10

|  | Formulation 10 |
|---|---|
| $D_{2\ h,\ 200\ rpm} - D_{2\ h,\ 50\ rpm}(\%)$ | 5.8 |
| $D_{2\ h,\ 200\ rpm} / D_{2\ h,\ 50\ rpm}$ | 1.4 |

<Test Results>

As shown in Table 14 and FIG. 21, the tablets of formulation 10 were hardly influenced by the rotation rate in the acidic solution. Moreover, as shown in FIG. 22, it was demonstrated that the tablets of formulation 10 had prolonged and favorable dissolution properties in the neutral solution. Furthermore, the bioavailability (BA) of the tablets of formulation 10 in dogs exhibited performance as high as 1.42 times that of the existing sustained-release preparation (Coreg CR) containing compound (2), and change in the plasma concentration of the drug showed preferable prolonged values for sustained-release preparations.

Example 9

Tablets having formulation 11a shown in Table 15 were produced by mixing of each component using a mortar followed by the direct compression method and subjected to the dissolution test in an acidic solution. The results are shown in Table 16 and FIG. 23.

TABLE 15

|  | Content (mg) | |
|---|---|---|
|  | Formulation 11a | Formulation 11b |
| Theophylline | 8.0 | 36.4 |
| HPC-H fine | 60.0 | 60.0 |
| HPC-SL regular | 9.0 | 7.5 |

TABLE 15-continued

|  | Content (mg) | |
|---|---|---|
|  | Formulation 11a | Formulation 11b |
| HPMCAS-LF | 90.0 | 90.0 |
| Povidone | 93.6 | 93.6 |
| Total | 260.6 | 287.5 |

TABLE 16

Influence of paddle rotation rate in acidic test medium on tablets having formulation 11a

|  | Formulation 11a |
|---|---|
| $D_{2\ h,\ 200\ rpm} - D_{2\ h,\ 50\ rpm}(\%)$ | 1.1 |
| $D_{2\ h,\ 200\ rpm} / D_{2\ h,\ 50\ rpm}$ | 1.0 |

<Test Results>

It was demonstrated that the tablets of formulation 11a were hardly influenced by rotation during dissolution in the acidic solution.

Preparation Example

Tablets having formulations 11b, 12a, and 12b shown in Table 17 are produced by mixing of each component using a mortar followed by the direct compression method.

TABLE 17

|  | Content (mg) | | |
|---|---|---|---|
|  | Formulation 11b | Formulation 12a | Formulation 12b |
| Theophylline | 36.4 | — | — |
| Probcol | — | 8.0 | 36.4 |
| HPC-H fine | 60.0 | 60.0 | 60.0 |
| HPC-SL regular | 7.5 | 8.9 | 8.9 |
| HPMCAS-LF | 90.0 | 90.0 | 90.0 |
| Povidone | 93.6 | 93.6 | 93.6 |
| Total | 287.5 | 260.5 | 288.9 |

INDUSTRIAL APPLICABILITY

The present invention can be used in the production of a sustained-release matrix preparation containing a pharmacologically active drug, for example, compound (1) or a salt thereof, or a hydrate thereof.

The invention claimed is:

1. The sustained-release matrix preparation comprising:
    (A) a pharmacologically active drug,
    (B) a combination of cellulose derivatives consisting of:
        (i) hydroxy propyl methylcellulose acetate succinate,
        (ii) hydroxy propyl cellulose having a viscosity of 150 to 400 mPa·s and/or 1000 to 4000 mPa·s, and
        (iii) hydroxypropyl cellulose having a viscosity of 3.0 to 5.9 mPa·s, and
    (C) mannitol,
    wherein, when the preparation is subjected to a dissolution test by the paddle method at rotation rates of 50 rpm and 200 rpm at 37±0.5° C. for 2 hours in 0.01 N hydrochloric acid, the preparation exhibits a difference in average percentage dissolution (value at the rotation rate of 200 rpm in the paddle method–value at the rotation rate of 50 rpm in the paddle method) of the pharmacologically active drug in the dissolution test medium of 10% or lower, or exhibits an average percentage dissolution ratio (value at the rotation rate of 200 rpm in the paddle method/value at the rotation rate of 50 rpm in the paddle method) of the pharmacologically active drug in the dissolution test medium of 2.0 or lower.

2. The sustained-release matrix preparation comprising:
(A) a pharmacologically active drug,
(B) a combination of cellulose derivatives consisting of:
   (i) hydroxy propyl methylcellulose acetate succinate,
   (ii) hydroxy propyl cellulose having a viscosity of 150 to 400 mPa·s and/or 1000 to 4000 mPa·s, and
   (iii) hydroxypropyl cellulose having a viscosity of 3.0 to 5.9 mPa·s, and
(C) mannitol,
wherein, when the preparation is subjected to a dissolution test by the paddle method at rotation rates of 50 rpm and 200 rpm at 37±0.5° C. for 2 hours in 0.01 N hydrochloric acid, the preparation exhibits a difference in average percentage dissolution (value at the rotation rate of 200 rpm in the paddle method–value at the rotation rate of 50 rpm in the paddle method) of the pharmacologically active drug in the dissolution test medium of 5% or lower.

3. The sustained-release matrix preparation comprising:
(A) a pharmacologically active drug,
(B) a combination of cellulose derivatives consisting of:
   (i) hydroxypropyl methylcellulose acetate succinate,
   (ii) hydroxy propyl cellulose having a viscosity of 150 to 400 mPa·s and/or 1000 to 4000 mPa·s, and
   (iii) hydroxypropyl cellulose having a viscosity of 3.0 to 5.9 mPa·s, and
(C) mannitol,
wherein, when the preparation is subjected to a dissolution test by the paddle method at rotation rates of 50 rpm and 200 rpm at 37±0.5° C. for 2 hours in 0.01 N hydrochloric acid, the preparation exhibits an average percentage dissolution ratio (value at the rotation rate of 200 rpm in the paddle method/value at the rotation rate of 50 rpm in the paddle method) of the pharmacologically active drug in the dissolution test medium of 1.5 or lower.

* * * * *